US010774385B2

(12) United States Patent
Kerr et al.

(10) Patent No.: US 10,774,385 B2
(45) Date of Patent: Sep. 15, 2020

(54) METHOD OF DETERMINING RISK OF 5-FLUOROURACIL TOXICITY

(71) Applicant: Oxford University Innovation Limited, Oxford (GB)

(72) Inventors: David Kerr, Oxford (GB); Ian Tomlinson, Oxford (GB); Dan Rosmarin, Oxford (GB); Claire Palles, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/123,620

(22) PCT Filed: Mar. 2, 2015

(86) PCT No.: PCT/GB2015/050597
§ 371 (c)(1),
(2) Date: Sep. 2, 2016

(87) PCT Pub. No.: WO2015/132569
PCT Pub. Date: Sep. 11, 2015

(65) Prior Publication Data
US 2017/0073765 A1    Mar. 16, 2017

(30) Foreign Application Priority Data
Mar. 4, 2014 (GB) .................... 1403820.2

(51) Int. Cl.
C12Q 1/68     (2018.01)
C12Q 1/6886   (2018.01)

(52) U.S. Cl.
CPC ..... *C12Q 1/6886* (2013.01); *C12Q 2600/106* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

2006/0051764 A1* 3/2006 Mandola .............. 435/6.14
2010/0240548 A1* 9/2010 Eidens ............... C12Q 1/6883 506/9

FOREIGN PATENT DOCUMENTS

| CN | 102575289 | 11/2012 |
| CN | 102770140 | 11/2012 |
| CN | 201580011724.9 | 1/2019 |
| CN | 201580011724.9 | 10/2019 |
| CN | 201580011724.9 | 4/2020 |
| EP | 15709982.1 | 10/2016 |
| EP | 15709982.1 | 1/2019 |
| GB | 1403820.2 | 11/2014 |
| IN | 201617028597 | 7/2020 |
| WO | WO95/111995 | * 5/1995 |
| WO | 2004/037852 | 5/2004 |
| WO | 2013/170215 | 11/2013 |
| WO | PCT/GB2015/050597 | 6/2015 |

OTHER PUBLICATIONS

Loganayagann et al. (British Journal of Cancer Jun. 4, 2013 vol. 108 p. 2505) (Year: 2013).*
Jennings et al. (PLOS ONE Oct. 2013 p. e78053) (Year: 2013).*
Rosmarin et al. (Journal of clinical oncology electronically published Mar. 3, 2014, vol. 32 p. 1031) (Year: 2014).*
Caudle, K.E. et al., "Clinical pharmacogenetics implementation consortium guidelines for dihydropyrimidine dehydrogenase genotype and fluoropyrimidine dosing", Clinical Pharmacology & Therapeutics, vol. 94, No. 6, pp. 640-645, (2013).
Garcia-Gonzalez, X. et al., "Variants in CDA and 4BCB1 are predictors of capecitabine-related adverse reactions in colorectal cancer", Oncotarget, vol. 6, No. 8, pp. 6422-6430, (2015).
Lecomte, T. et al., "Thymidylate synthase gene polymorphism predicts toxicity in colorectal cancer patients receiving 5-Fluorouracil-based chemotherapy", Clinical Cancer Research, vol. 10, pp. 5880-5888, (2004).
Lin, X. et al., "Risk prediction of prevalent diabetes in a Swiss population using a weighted genetic score—the CoLaus Study", Diabetologia, vol. 52, pp. 600-608, (2009).
U.K. Search Report dated Nov. 27, 2014 for GB application No. GB1403820.2.
Rosmarin, D. et al., "A candidate gene study of capecitabine-related toxicity in colorectal cancer identifies new toxicity variants at DPYD and a putative role for ENOSF1 rather than TYMS", Gut, vol. 64, No. 1, pp. 111-120, (2015).
Saif, M.W., "Dihydropyrimidine dehydrogenase gene (DPYD) polymorphism among Caucasian and non-Caucasian patients with 5-FU- and capecitabine-related toxicity using full sequencing of DPYD", Cancer Genomics & Proteomics, vol. 10, pp. 89-92, (2013).
Rosmarin, D. et al., "Genetic markers of toxicity from capecitabine and other fluorouracil-based regimens: Investigation in the QUASAR2 study, systematic review, and meta-analysis", Journal of Clinical Oncology, vol. 32, No. 10, pp. 1031-1039, (2014).
Sharma, R. et al., "Thymidylate synthase and methylenetetrahydrofolate reductase gene polymorphisms and toxicity to capecitabine in advanced colorectal cancer patients", Clinical Cancer Research, vol. 14, No. 3, pp. 817-825, (2008).
Afzal, S. et al., "Combinations of polymorphisms in genes involved in the 5-Fluorouracil metabolism pathway are associated with gastrointestinal toxicity in chemotherapy-treated colorectal cancer patients", Clinical Cancer Research, vol. 17, No. 11, pp. 3822-3829, (2011).
Ghosh, S. et al., "Analysis of polymorphisms and haplotype structure of the human thymidylate synthase genetic region: A tool for pharmacogenetic studies", PloS one, vol. 7, Issue 4, pp. 1-8, (2012).

(Continued)

*Primary Examiner* — Katherine D Salmon
(74) *Attorney, Agent, or Firm* — Evan Law Group LLC

(57) ABSTRACT

The invention provides an assay useful in predicting risk of 5-fluorouracil (FU) toxicity in a subject. The subject may be screened for the presence of at least one TYMS polymorphism and/or at least one DPYD polymorphism. Suitable TYMS and DPYD polymorphisms are provided. The presence of one or more of the polymorphisms indicates an increased risk of developing FU toxicity; a negative result may indicate a decreased risk of developing FU toxicity.

9 Claims, 8 Drawing Sheets

(56) References Cited

OTHER PUBLICATIONS

Figure 1:
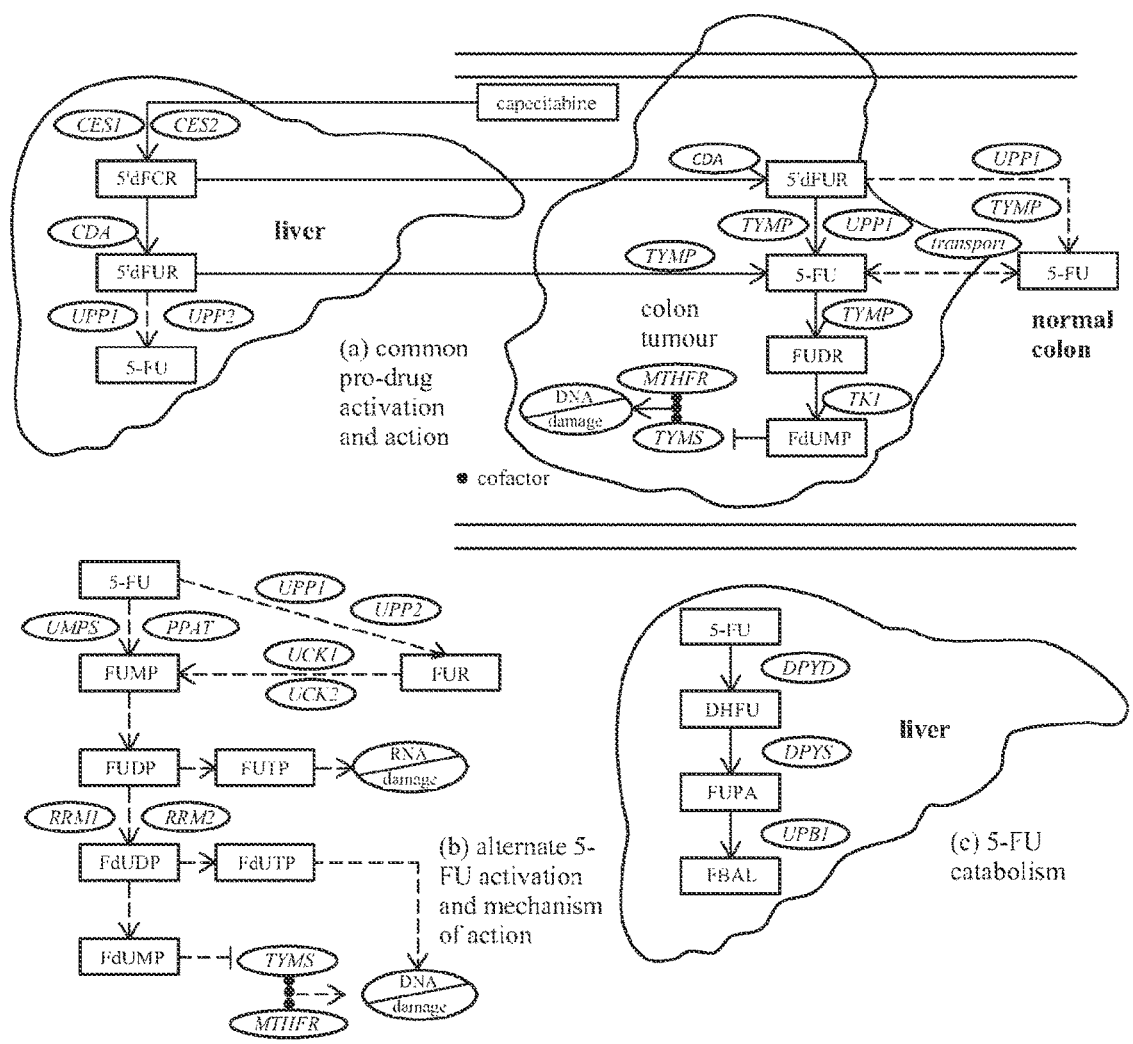

De Gramont, A. et al., "Leucovorin and fluorouracil with or without oxaliplatin as first-line treatment in advanced colorectal cancer", Journal of Clinical Oncology, vol. 18, No. 16, pp. 2938-2947, (2000).
Cassidy, J. et al., "XELOX (capecitabine plus oxaliplatin): Active first-line therapy for patients with metastatic colorectal cancer", Journal of Clinical Oncology, vol. 22, No. 11, pp. 2084-2091, (2004).
Douillard, J.Y. et al., "Irinotecan combined with fluorouracil compared with fluorouracil alone as first-line treatment for metastatic colorectal cancer: a multicentre randomised trial", The Lancet, vol. 355, No. 9209, pp. 1041-1047, (2000).
Noordhuis, P. et al., "A non-radioactive sensitive assay to measure 5-fluorouracil incorporation into DNA of solid tumors", Nucleosides, Nucleotides & Nucleic Acids, vol. 23, No. 8-9, pp. 1481-1484, (2004).
Grem, J.L., "5-fluorouracil: forty-plus and still ticking. A review of its preclinical and clinical development", Investigational New Drugs, vol. 18, No. 4, pp. 299-313, (2000).
Twelves, C. et al., "Capecitabine as adjuvant treatment for stage III colon cancer", The New England Journal of Medicine, vol. 352, No. 26, pp. 2696-2704, (2005).
Saltz, L.B. et al., "Irinotecan fluorouracil plus leucovorin is not superior to fluorouracil plus leucovorin alone as adjuvant treatment for stage III colon cancer: Results of CALGB 89803", Journal of Clinical Oncology, vol. 25, No. 23, pp. 3456-3461, (2007).
Stein, B.N. et al., "Age and sex are independent predictors of 5-fluorouracil toxicity: Analysis of a large scale phase III trial", Cancer, vol. 75, No. 1, pp. 11-17, (1995).
Cassidy, J. et al., "First-line oral capecitabine therapy in metastatic colorectal cancer: a favorable safety profile compared with intravenous 5-fluorouracil/leucovorin", Annals of Oncology, vol. 13, No. 4, pp. 566-575, (2002).
Haller, D.G. et al., "Potential regional differences for the tolerability profiles of fluoropyrimidines", Journal of Clinical Oncology, vol. 26, No. 13, pp. 2118-2123, (2008).
Boisdron-Celle, M. et al., "5-fluorouracil-related severe toxicity: A comparison of different methods for the pretherapeutic detection of dihydropyrimidine dehydrogenase deficiency", Cancer Letters, vol. 249, No. 2, pp. 271-282, (2007).
Saif, M.W. et al., "Pharmacokinetically guided dose adjustment of 5-fluorouracil: A rational approach to improving therapeutic outcomes", Journal of the National Cancer Institute, vol. 101, No. 22, pp. 1543-1552, (2009).
Longley, D.B. et al., "5-fluorouracil: Mechanisms of action and clinical strategies", Nature Reviews Cancer, vol. 3, No. 5, pp. 330-338, (2003).
Thorn, C.F. et al., "PharmGKB summary: fluoropyrimidine pathways", Pharmacogenet Genomics, vol. 21, No. 4, pp. 237-242, (2011).
West, C.M.L. et al., "The potential of positron-emission tomography to study anticancer-drug resistance", Nature Reviews Cancer, vol. 4, No. 6, pp. 457-469, (2004).
Miwa, M. et al., "Design of a novel oral fluoropyrimidine carbamate, capecitabine, which generates 5-fluorouracil selectively in tumours by enzymes concentrated in human liver and cancer tissue", European Journal of Cancer, vol. 34, No. 8, pp. 1274-1281, (1998).
Van Kuilenburg, A.B.P. et al., "Heterozygosity for a point mutation in an invariant splice donor site of dihydropyrimidine dehydrogenase and severe 5-fluorouracil related toxicity", European Journal of Cancer, vol. 33, No. 13, pp. 2258-2264, (1997).
Mandola, M.V. et al., "A novel single nucleotide polymorphism within the 5' tandem repeat polymorphism of the thymidylate synthase gene abolishes USF-1 binding and alters transcriptional activity", Cancer Research, vol. 63, No. 11, pp. 2898-2904, (2003).

Zhang, Q. et al., "Associations between gene polymorphisms of thymidylate synthase with its protein expression and chemosensitivity to 5-fluorouracil in pancreatic carcinoma cells", Chinese Medical Journal, vol. 124, No. 2, pp. 262-267, (2011).
Purcell, S. et al., "PLINK: A tool set for whole-genome association and population-based linkage analyses", The American Journal of Human Genetics, vol. 81, No. 3, pp. 559-575, (2007).
Kerr, D. "Quasar 2", University of Oxford, Department of Oncology, pp. 1-7, found at www.oncology.ox.ac.uk/trial/quasar-2, printed on Jun. 20, 2017.
Schwab, M. et al., "Role of genetic and nongenetic factors for fluorouracil treatment-related severe toxicity: A prospective clinical trial by the German 5-FU toxicity study group", Journal of Clinical Oncology, vol. 26, No. 13, pp. 2131-2138, (2008).
Cohen, V. et al., "Methylenetetrahydrofolate reductase polymorphism in advanced colorectal cancer: A novel genomic predictor of clinical response to fluoropyrimidine-based chemotherapy", Clinical Cancer Research, vol. 9, No. 5, pp. 1611-1615, (2003).
Largillier, R. et al., "Pharmacogenetics of capecitabine in advanced breast cancer patients", Clinical Cancer Research, vol. 12, No. 18, pp. 5496-5502, (2006).
Morel, A. et al., "Clinical relevance of different dihydropyrimidine dehydrogenase gene single nucleotide polymorphisms on 5-fluorouracil tolerance", Molecular Cancer Therapeutics, vol. 5, No. 11, pp. 2895-2904, (2006).
Gross, E. et al., "Strong association of a common dihydropyrimidine dehydrogenase gene polymorphism with fluoropyrimidine-related toxicity in cancer patients", PloS One, vol. 3, No. 12, pp. 1-7, (2008).
Salgado, J. et al., "Polymorphisms in the thymidylate synthase and dihydropyrimidine dehydrogenase genes predict response and toxicity to capecitabine-raltitrexed in colorectal cancer", Oncology Reports, vol. 17, No. 2, pp. 325-328, (2007).
Capitain, O. et al., "The influence of fluorouracil outcome parameters on tolerance and efficacy in patients with advanced colorectal cancer", The Pharmacogenomics Journal, vol. 8, No. 4, pp. 256-267, (2008).
Martinez-Balibrea, E. et al., "Pharmacogenetic approach for capecitabine or 5-fluorouracil selection to be combined with oxaliplatin as first-line chemotherapy in advanced colorectal cancer", European Journal of Cancer, vol. 44, No. 9, pp. 1229-1237, (2008).
Ribelles, N. et al., "A carboxylesterase 2 gene polymorphism as predictor of capecitabine on response and time to progression", Current Drug Metabolism, vol. 9, No. 4, pp. 336-343, (2008).
Ruzzo, A. et al., "Pharmacogenetic profiling in patients with advanced colorectal cancer treated with first-line FOLFIRI chemotherapy", The Pharmacogenomics Journal, vol. 8, No. 4, pp. 278-288, (2008).
Afzal, S. et al., "MTHFR polymorphisms and 5-FU-based adjuvant chemotherapy in colorectal cancer", Annals of Oncology, vol. 20, No. 10, pp. 1660-1666, 2009).
Braun, M.S. et al., "Association of molecular markers with toxicity outcomes in a randomized trial of chemotherapy for advanced colorectal cancer: The FOCUS trial", Journal of Clinical Oncology, vol. 27, No. 33, pp. 5519-5528, (2009).
Chua, W. et al., "Molecular markers of response and toxicity to FOLFOX chemotherapy in metastatic colorectal cancer", British Journal of Cancer, vol. 101, No. 6, pp. 998-1004, (2009).
Derwinger, K. et al., "A study of the MTHFR gene polymorphism C677T in colorectal cancer", Clinical Colorectal Cancer, vol. 8, No. 1, pp. 43-48, (2009).
Gusella, M. et al., "Predictors of survival and toxicity in patients on adjuvant therapy with 5-fluorouracil for colorectal cancer", British Journal of Cancer, vol. 100, No. 10, pp. 1549-1557, (2009).
Goekkurt, E. et al., "Pharmacogenetic analyses of a phase III trial in metastatic gastroesophageal adenocarcinoma with fluorouracil and leucovorin plus either oxaliplatin or cisplatin: A study of the arbeitsgemeinschaft internistische onkologie", Journal of Clinical Oncology, vol. 27, No. 17, pp. 2863-2873, (2009).
Boige, V. et al., "Pharmacogenetic assessment of toxicity and outcome in patients with metastatic colorectal cancer treated with LV5FU2, FOLFOX, and FOLFIRI: FFCD 2000-05", Journal of Clinical Oncology, vol. 28, No. 15, pp. 2556-2564, (2010).

(56) References Cited

OTHER PUBLICATIONS

Etienne-Grimaldi, M-C. et al., "Methylenetetrahydrofolate reductase (MTHFR) gene polymorphisms and FOLFOX response in colorectal cancer patients", British Journal of Clinical Pharmacology, vol. 69, No. 1, pp. 58-66, (2010).
Martinez-Balibrea, E. et al., "UGT1A and TYMS genetic variants predict toxicity and response of colorectal cancer patients treated with first-line irinotecan and fluorouracil combination therapy", British Journal of Cancer, vol. 103, No. 4, pp. 581-589, (2010).
McLeod, H.L. et al., "Pharmacogenetic predictors of adverse events and response to chemotherapy in metastatic colorectal cancer: Results from north American gastrointestinal intergroup trial N9741", Journal of Clinical Oncology, vol. 28, No. 20, pp. 3227-3233, (2010).
Zarate, R. et al., "Oxaliplatin, irinotecan and capecitabine as first-line therapy in metastatic colorectal cancer (mCRC): a dose-finding study and pharmacogenomic analysis", British Journal of Cancer, vol. 102, No. 6, pp. 987-994, (2010).
Caronia, D. et al., "A polymorphism in the cytidine deaminase promoter predicts severe capecitabine-induced hand-foot syndrome", Clincal Cancer Research, vol. 17, No. 7, pp. 2006-2013, (2011).
Deenen, M.J. et al., "Relationship between single nucleotide polymorphisms and haplotypes in DPYD and toxicity and efficacy of capecitabine in advanced colorectal cancer", Clinical Cancer Research, vol. 17, No. 10, pp. 3455-3468, (2011).
Glimelius, B. et al., "Prediction of irinotecan and 5-fluorouracil toxicity and response in patients with advanced colorectal cancer", the Pharmacogenomics Journal, vol. 11, No. 1, pp. 61-71, (2011).
Dunlop, M.G. et al., "Common variation near CDKN1A, POLD3 and SHROOM2 influences colorectal cancer risk", Nature Genetics, vol. 44, No. 7, pp. 770-776, (2012).
Cuppen, E. "Genotyping by allele-specific amplification (KASPar)", CSH Protocols, pdb prot4841, 2 pages, (2007).
Horie, N. et al., "Functional analysis and DNA polymorphism of the tandemly repeated sequences in the 5'-terminal regulatory region of the human gene for thymidylate synthase", Cell Structure and Function, vol. 20, No. 3, pp. 191-197, (1995).
Dotor, E. et al., "Tumor thymidylate synthase 1494del6 genotype as a prognostic factor in colorectal cancer patients receiving fluorouracil-based adjuvant treatment", Journal of Clinical Oncology, vol. 24, No. 10, pp. 1603-1611, (2006).
Van Kuilenburg, A.B. P. et al., "Novel disease-causing mutations in the dihydropyrimidine dehydrogenase gene interpreted by analysis of the three-dimensional protein structure", The Biochemical Journal, vol. 364, pt. 1, pp. 157-163, (2002).
Van Kuilenburg, A.B.P. et al., "Genotype and phenotype in patients with dihydropyrimidine dehydrogenase deficiency", Human Genetics, vol. 104, No. 1, pp. 1-9, (1999).
Offer, S.M. et al., "Phenotypic profiling of DPYD variations relevant to 5-fluorouracil sensitivity using real-time cellular analysis and in vitro measurement of enzyme activity", Cancer Research, vol. 73, No. 6, pp. 1958-1968, (2013).
Seck, K. et al., "Analysis of the DPYD gene implicated in 5-fluorouracil catabolism in a cohort of Caucasian individuals", Clinical Cancer Research, vol. 11, No. 16, pp. 5886-5892, (2005).
Van Kuilenburg, A.B.P. et al., "Clinical implications of dihydropyrimidine dehydrogenase (DPD) deficiency in patients with severe 5-fluorouracil-associated toxicity: Identification of new mutations in the DPD gene", Clinical Cancer Research, vol. 6, No. 12, pp. 4705-4712, (2000).
Abuli, A. et al., "Genetic susceptibility variants associated with colorectal cancer prognosis", Carcinogenesis, vol. 34, No. 10, pp. 2286-2291, (2013).
Goldstein, J.I. et al., "Zcall: a rare variant caller for array-based genotyping", Bioinformatics, vol. 28, No. 19, pp. 2543-2545, (2012).

Delaneau, O. et al., "Improved whole-chromosome phasing for disease and population genetic studies", Nature Methods, vol. 10, No. 1, pp. 5-6, (2013).
Howie, B. et al., "Fast and accurate genotype imputation in genome-wide association studies through pre-phasing", Nature Genetics, vol. 44, No. 8, pp. 955-959, (2012).
Marchini, J. et al., "A new multipoint method for genome-wide association studies by imputation of genotypes", Nature Genetics, vol. 39, No. 7, pp. 906-913, (2007).
Roche, "454 sequencing system guidelines for amplicon experimental design", 454 Life Sciences Corporation, pp. 1-50, (2011).
Magi, R. et al., "GWAMA: software for genome-wide association meta-analysis", BMC Bioinformatics, vol. 11, No. 288, pp. 1-6, (2010).
Yang, T-P. et al., "Genevar: a database and java application for the analysis and visualization of SNP-gene associations in eQTL studies", Bioinformatics, vol. 26, No. 19, pp. 2474-2476, (2010).
Li, Q. et al., "Integrative eQTL-based analyses reveal the biology of breast cancer risk loci", Cell, vol. 152, No. 3, pp. 633-641, (2013).
Nica, A.C. et al., "The architecture of gene regulatory variation across multiple human tissues: The MuTHER study", Plos Genetics, vol. 7, No. 2, (2011).
Stranger, B.E. et al., "Patterns of Cis regulatory variation in diverse human populations", Plos Genetics, vol. 8, No. 4, pp. 272-284, (2012).
Dimas, A.S. et al., "Common regulatory variation impacts gene expression in a cell type dependent manner", Science, vol. 325, No. 5945, pp. 1246-1250, (2009).
Dolnick, B.J. et al., "A novel function for the rTS gene", Cancer Biology & Therapy, vol. 2, issue 4, pp. 364-369, (2003).
Van Kuilenburg, A.B.P. et al., "Identification of three novel mutations in the dihydropyrimidine dehydrogenase gene associated with altered pre-mRNA splicing or protein function", Biological Chemistry, vol. 386, No. 4, pp. 319-324, (2005).
Kerr, D.J., "Multicentre international study of capecitabine ± bevacizumab as adjuvant treatment of colorectal cancer", ISRCTN registry, pp. 1-8, found at www.isrctn.com/ISRCTN45133151, printed on Jun. 19, 2017.
International Search Report and Written Opinion dated Oct. 6, 2015 for PCT application No. PCT/GB2015/050597, 11 pages.
International Preliminary Report on Patentability dated Sep. 6, 2016 for PCT application No. PCT/GB2015/050597, 7 pages.
Church, D. et al., ""Toxgnostics": an unmet need in cancer medicine", Nature Reviews Cancer, vol. 14, pp. 440-445, (2014).
Fernandez-Rozadilla, C. et al., "Pharmacogenomics in colorectal cancer: a genome-wide association study to predict toxicity after 5-fluorouracil or FOLFOX administration", The Pharmacogenomics Journal, vol. 13, pp. 209-217, (2013).
Loganayagam, A. et al., "Pharmacogenetic variants in the DPYD, TYMS, CDA and MTHFR genes are clinically significant predictors of fluoropyrimidine toxicity", British Journal of Cancer, vol. 108, pp. 2505-2515, (2013).
Van Staveren, M.C. et al., "Evaluation of predictive tests for screening for dihydropyrimidine dehydrogenase deficiency", The Pharmacogenomics Journal, vol. 13, pp. 389-395, (2013).
Terrazzino, S. et al., "DPYD IVS14+1G>A and 2846A>T genotyping for the prediction of severe fluoropyrimidine-related toxicity: a meta-analysis", Pharmacogenomics, vol. 14, No. 11, pp. 1255-1272, (2013).
Vreken, P. et al., "Dihydropyrimidine dehydrogenase (DPD) deficiency: identification and expression of missense mutations C29R, R886H and R235W", Human Genetics, vol. 101, pp. 333-338, (1997).
PCT Application No. 15 709 982.1, dated Jan. 16, 2018.
Lee, A.M. et al., "Genetic biomarkers for fluorouracil toxicity predication: The long road to clinical utility", Journal of Clinical Oncology, vol. 32, No. 10, pp. 989-990, (2014).

* cited by examiner

METHOD OF DETERMINING RISK OF 5-FLUOROURACIL TOXICITY

The present invention relates to an assay. More specifically, the invention relates to an assay useful in predicting toxicity of a chemotherapeutic agent. Reagents and kits for carrying out the assay are described.

5-fluorouracil (FU) is frequently used as a chemotherapeutic agent for treatment of cancers such as colorectal cancer (CRC), breast cancer and other solid tumours. FU-based regimens include bolus and infusional intravenous administration, and oral capecitabine, a prodrug that undergoes preferential conversion to FU in malignant tissue. A common treatment for patients with CRC is Capecitabine (pentyl [1-(3,4-dihydroxy-5-methyltetrahydrofuran-2-yl)-5-fluoro-2-oxo-1H-pyrimidin-4-yl]carbamate).

The addition of oxaliplatin or irinotecan to FU can improve efficacy, and the combination regimens FOLFOX (de Gramont A et al., *J Clin Oncol* 18(16): 2938-47 (2000), incorporated herein by reference), XELOX (Cassidy J et al., *J Clin Oncol* 22(11): 2084-91 (2004), incorporated herein by reference) and FOLFIRI (Douillard J Y et al., *Lancet* 355 (9209): 1041-7 (2000), incorporated herein by reference) are standard therapies for the treatment of cancer.

FU is thus a mainstay of chemotherapy. However, FU toxicities are common, with 10-30% of patients suffering substantial toxicities, defined as Grade 3 or above as measured using the NCI Common Toxicity Criteria for Adverse Events (CTCAE) version 3.0):

| CTCAE v.3.0 | |
|---|---|
| GRADE | MEANING |
| 1 | Mild Adverse Event |
| 2 | Moderate Adverse Event |
| 3 | Severe Adverse Event |
| 4 | Life-threatening or disabling Adverse Event |
| 5 | Death related to Adverse Event |

Capecitabine causes cytotoxicity by inhibiting production of thymidine and by being converted to metabolites that are incorporated into DNA and RNA (Noordhuis P et al., Nucleosides Nucleotides & Nucleic Acids 23: 1481-1484 (2004), incorporated herein by reference). As with other 5-FU-based chemotherapy regimens, approximately one third of capecitabine patients suffer dose-limiting levels of drug-induced adverse events.

FU toxicities typically include symptoms such as diarrhea, nausea and vomiting, mucositis/stomatitis, myelosuppression, neutropaenia, thrombocytopaenia, and hand-foot syndrome (HFS). The most common dose-limiting capecitabine toxicities are HFS and diarrhea. There is wide variation in the frequency and type of toxicity depending upon the schedule of administration, and overall there is a 0.5-1.0% mortality (Grade 5 as measured using CTCAE version 3.0) associated with FU use (Grem J L., *Investigational new drugs* 18(4): 299-313 (2000); and Twelves C et al., *The New England journal of medicine* 352(26): 2696-704 (2005), both incorporated herein by reference). The onset of toxicity may be rapid, which results in mortality for 0.5% to 2% of patients in monotherapy and combination regimens of infusional and bolus 5-FU (Saltz L B et al., *J Clin Oncol*. 25(23): 3456-3461 (2007) incorporated herein by reference), and about half that number for capecitabine schedules. Inter-patient differences in toxicity may be explained by clinical factors such as patient age, gender, local clinical practice and diet (Stein B N et al., *Cancer* 75(1): 11-17 (1995); Cassidy J et al,. *Ann Oncol*. 13(4): 566-575 (2002); Haller D G et al., *J Clin Oncol*. 26(13): 2118-2123 (2008), each incorporated herein by reference). However, much variability in toxicity remains unexplained.

Consequently, much attention has focused on the identification of biomarkers or assays predictive of FU toxicity (Boisdron-Celle M et al., *Cancer letters* 249(2): 271-82 (2007); and Saif M W et al., *Journal of the National Cancer Institute* 101(22): 1543-52 (2009), both incorporated herein by reference). However, FU metabolism is complex, with multiple enzymatic reactions and intermediates, as shown in FIG. 1.

The biochemical pathway of capecitabine activation and subsequent 5-FU action and degradation is well-established and provides 25 candidate genes in which variation might affect 5-FU toxicity (FIG. 1) (Longley D B et al., *Nat Rev Cancer* 3(5): 330-338 (2003); Thorn C F et al., *Pharmacogenet Genomics* 21(4): 237-242 (2011); West C M et al., *Nat Rev Cancer* 4(6): 457-469 (2004); Miwa M et al., *Eur J Cancer* 34(8): 1274-1281 (1998), each incorporated herein by reference). Upon absorption in the gut, capecitabine is partially converted to 5-FU in the liver, then preferentially converted to 5-FU at the CRC site. Much 5-FU is degraded in the liver by dihydropyrimidine dehydrogenase (DPYD) prior to activation. As part of the drug's rationally-designed activation, 5-FU is further activated in the tumour to cytotoxic compounds that inhibit DNA synthesis by competing with nucleotide precursors for binding with thymidylate synthase (TYMS). Various sources of toxicity may exist, including alternative activation pathways outside the tumour that result in direct DNA/RNA damage through incorporation, undesired transport of activated compounds, variable expression of drug targets, and reduced levels of drug degradation.

In a previous study, severe dihydropyrimidine dehydrogenase (DPYD) deficiency has been linked with lethal FU use (Van Kuilenburg A B et al., *Eur J Cancer* 33(13): 2258-64 (1997), incorporated herein by reference). Since then, an expanding number of polymorphisms and rare variants in genes involved in FU metabolism have been suggested as influencing the risk of adverse events, including MTHFR 677C>T (Afzal S et al., *Clin Cancer Res* 17(11): 3822-9 (2011), incorporated herein by reference); and TYMS alleles (Lecomte T et al., *Clin Cancer Res* 10(17): 5880-8 (2004)), incorporated herein by reference). The TYMS risk alleles are common in the northern European population. However, despite some evidence that the TYMS alleles affect mRNA expression levels (Mandola M V et al., *Cancer research* 63(11): 2898-904 (2003); and Zhang Q et al., *Chinese medical journal* 124(2): 262-7 (2011), both incorporated herein by reference), the existing data are limited e.g. by inconsistency in reporting and testing of toxicities; by pooling of patients on different FU schedules; and by the combined analysis of functionally-distinct polymorphisms.

Commercially available kits aimed at identifying FU toxicity risk are not optimal and tend to identify common polymorphisms, thus classifying nearly every test subject as being at risk. Even kits which do not include such common polymorphisms typically provide no better than 29% sensitivity.

There is therefore currently no reliable way of predicting adverse events, since it is unclear which (if any) genetic variants make good predictors of FU toxicity.

There is accordingly a need for certainty regarding which genetic variants are truly predictive of adverse events from FU. There is a need for clinical biomarkers and assays predictive of FU toxicity.

The present invention addresses one or more of the above needs. In particular, the present inventors have discovered a combination of clinical biomarkers and related assays that are predictive of FU toxicity.

Accordingly, the invention provides a method of screening for risk of 5-fluorouracil (FU) toxicity in a subject, comprising screening the subject for the presence of at least one polymorphism selected from:
  a. a TYMS polymorphism selected from the group consisting of: 5'VNTR 2R/3R rs45445694, 3'UTR 6 bp ins-del rs16430 and rs2612091; and/or
  b. a DPYD polymorphism selected from the group consisting of: *2A rs3918290, 2846T>A rs67376798, rs12132152, rs12022243, rs7548189, p.Ala551 Thr
Functionally equivalent variants of the DPYD polymorphism may also be screened for.

A positive result (i.e. the presence of one or more of the above-mentioned polymorphisms) indicates an increased risk of developing FU toxicity. A negative result (i.e. absence of the screened-for polymorphisms) may indicate a decreased risk of developing FU toxicity.

In one embodiment, the invention provides a method of screening for risk of 5-fluorouracil (FU) toxicity in a subject, comprising screening the subject for the presence of at least one polymorphism selected from:
  a. a TYMS polymorphism selected from the group consisting of: 5'VNTR 2R/3R rs45445694, 3'UTR 6 bp ins-del rs16430 and rs2612091; and/or
  b. a DPYD polymorphism selected from the group consisting of: *2A rs3918290, 2846T>A rs67376798, rs12132152, rs12022243, rs7548189, p.Ala551Thr, and functionally equivalent variants thereof;
wherein the presence of said at least one polymorphism indicates an increased risk of developing FU toxicity compared to a subject which does not possess said at least one polymorphism.

In one embodiment, the invention provides a method of screening for risk of 5-fluorouracil (FU) toxicity in a subject, comprising screening the subject for the presence of at least one polymorphism selected from:
  a. a TYMS polymorphism selected from the group consisting of: 5'VNTR 2R/3R rs45445694, 3'UTR 6 bp ins-del rs16430 and rs2612091; and/or
  b. a DPYD polymorphism selected from the group consisting of: *2A rs3918290, 2846T>A rs67376798, rs12132152, rs12022243, rs7548189, p.Ala551Thr, and functionally equivalent variants thereof;
wherein a negative result indicates a decreased risk of developing FU toxicity compared to a subject which possesses said at least one polymorphism.

In one embodiment, the invention provides a method of screening for risk of 5-fluorouracil (FU) toxicity in a subject, comprising screening the subject for the presence of at least one polymorphism selected from:
  a. TYMS polymorphism selected from the group consisting of: 5'VNTR 2R/3R rs45445694, 3'UTR 6 bp ins-del rs16430 and rs2612091;
and/or
  b. DPYD polymorphism selected from the group consisting of: *2A rs3918290, 2846T>A rs67376798, rs12132152, rs12022243, rs7548189, p.Ala551Thr and functionally equivalent variants thereof;
wherein the presence of one or more of said polymorphisms indicates an increased risk of developing FU toxicity and a negative result indicates a decreased risk of developing FU toxicity.

The TYMS 5'VNTR 2R/3R polymorphism may be defined by rs45445694 and the 3'UTR 6 bp ins-del polymorphism by rs16430. The DPYD *2A polymorphism may be defined by rs3918290 and the 2846T>A polymorphism by rs67376798. The rs number refers to the dbSNP ID.

The above method is highly predictive of FU toxicity. The method may include screening for any combination of the above-mentioned polymorphisms. Thus screening may be for any of TYMS polymorphisms 5' 2R/3R, 3'UTR 6 bp ins-del and rs2612091, and any of DPYD polymorphisms *2A, 2846T>A, rs12132152, rs7548189, p.Ala551Thr and functionally equivalent variants thereof.

The method of the invention may comprise screening for the presence of TYMS polymorphism rs2612091; and DPYD polymorphisms *2A, 2846T>A, rs12132152, rs7548189, p.Ala551Thr. This method has surprisingly been found to provide up to 27% sensitivity, 91% specificity, 60% positive predictive value and 71% negative predictive value.

The method of the invention may comprising screening for the presence of TYMS polymorphisms 5'VNTR 2R/3R and 3'UTR 6 bp ins-del; and DPYD polymorphisms *2A and 2846T>A. The method has surprisingly been found to provide up to 58% sensitivity, 63% specificity, 47% positive predictive value (PPV) and 72% negative predictive value.

Thus, the methods of the invention represent a significant improvement on methods based on using commercially available kits.

The subject may be a cancer patient. The patient may have a solid tumour cancer such as colorectal cancer (CRC) or breast cancer. The subject may be undergoing (or have undergone) chemotherapy with FU. Alternatively, the method may be carried out on a subject who is about to undergo chemotherapy with FU.

The chemotherapy with FU may be a FU monotherapy, such as capecitabine monotherapy. The term "chemotherapy with FU" however includes any therapy based on FU either alone or in combination with one or more other agents, e.g. FOLFOX, XELOX, or FOLFIRI.

Screening for the presence of TYMS and/or DPYD polymorphisms may be carried out on a sample from the subject. This sample may be a fluid sample, such as a saliva, blood, serum or plasma sample. This sample may be a solid sample, such as a sample from a biopsy.

Screening for DPYD variants with equivalent functional effects to 2846A, *2A rs12132152, rs7548189 or p.Ala551Thr is also included within the scope of this invention. Such variants may be screened for using available gene sequencing or direct functional assays as are known in the technical field.

The method of the present invention permits close monitoring of a subject in which one or more of the above-mentioned polymorphisms are present and who is therefore at increased risk of toxicity. The method of the invention may accordingly include a step of monitoring the subject for symptoms of FU toxicity in the event of a positive result, i.e. where one or more of the above-mentioned polymorphisms is detected.

The FU toxicity risk may be high-grade FU toxicity, i.e. grade 3+ in accordance with the NCI Common Toxicity Criteria for Adverse Events (CTCAE) version 3.0. The high-grade FU toxicity may be global toxicity. The high-grade FU toxicity may include diarrhea, nausea and vomiting, mucositis/stomatitis, myelosuppression, neutropaenia, thrombocytopaenia, and hand-foot syndrome (HFS).

TYMS and DPYD polymorphisms may be identified using a score test, which tests for independent effects of variants within a region. This test may comprise performing logistic regression with toxicity for the number of high-risk alleles carried by an individual and correspondingly assigning the subject a genetic score (e.g. from 0 to 4). The following is an example, genetic risk score=$\Sigma \beta_i N_i$, where $\beta_i$ is the beta coefficient of the ith SNP significantly associated with global toxicity in a logistic regression model, and Ni is the number of harmful alleles carried by that individual at that locus.

DPYD polymorphisms may also be identified using a group test. This test may comprise a combined group assessment of rare variants in which, on the basis of enzyme function, carriers of either DPYD 2846A or DPYD *2A are classed as "variant" and others as "wild-type".

This assessment may include DPYD variants with equivalent functional effects to 2846A, *2A, rs12132152, rs7548189 and/or p.Ala551Thr.

The present invention also provides one or more reagents capable of detecting the presence of the above-mentioned TYMS and/or DPYD polymorphisms e.g. in a sample obtained from a patient, for use in the method of the invention.

The above-mentioned reagents may be present in a kit. Accordingly, the present invention provides a kit comprising one or more of the above-mentioned reagents capable of detecting the presence of the above-mentioned TYMS and/or DPYD polymorphisms.

The screening for the presence of at least one polymorphism may comprise sequencing methods known in the art such as PCR.

List of Tables

Table 1: Associations Between Select DPYD and TYMS Polymorphisms and Capecitabine-Related Toxicity (Allelic Model, Grade 0-2 v 3+ Toxicity)

Fixed effect meta-analysis and pooled logistic analysis results are shown for two TYMS and two DPYD variants, for patients given capecitabine. Individual effects of each polymorphism are provided first, in which the odds ratio (OR) describes the increased proportion of patients experiencing grade 3+ toxicity (global, diarrhea or HFS), per toxicity allele held (range 0-2 alleles per patient). For the two TYMS polymorphisms, logistic models show that both polymorphisms contribute to a patient's risk. This risk is assessed by meta-analysis of the TYMS "score" test, in which the OR shows the increased proportion of patients experiencing high toxicity per putative toxicity allele held from either the 5'VNTR or 3'UTR polymorphism (range 0-4 alleles per patient). For the functional DPYD polymorphisms, the OR shows the effect of having either the *2A or 2846 rare allele. N=total number of patients studied, TAF=frequency of the putative toxicity-associated allele, and S=number of studies. Test alleles shown in italics.

Table 2: QUASAR2 Patient Characteristics

The patient characteristics from the QUASAR2 study population are shown for 1046 individuals in total, randomised to receive capecitabine alone (47%) or capecitabine and bevacizumab (53%), including numbers of Grade 3+ toxic events.

Table 3: Toxicity Frequencies in QUASAR2

Toxicity frequencies for the QUASAR2 study are shown from grade 0-4, including unreported grade.

Table 4: Toxicity Frequencies in SCP Study

Patients for this set were selected for high and low toxicity (i.e., few grade 2) and only diarrhea and HFS toxicity data were collected.

Table 5: Candidate Gene Region Summary 25 candidate capecitabine/5-FU pathway genes, from which variants were identified that were present on one or more of the Hap300/370, Hap610 or exome arrays.

Table 6: Selected Associations Between Genetic Variants and Capecitabine Toxicity in QUASAR2

Associations are shown for global and selected individual toxicities measured as binary or continuous variables. TAF is the frequency of the toxicity-associated allele. The first row of each results cell is an OR, the second the 95% CIs and the third the p-value for the per allele model.

Table 7: Testing TYMS Rs2612091, 5' VNTR and 3'UTR Haplotypes for Independent Effects of One Polymorphism Haplotype analyses were performed in PLINK (Purcell S et al., *American Journal of Human Genetics* 81(3): 559-75 (2007) incorporated herein by reference) using the "—independent-effect" command, in which for each polymorphism in turn, alleles are analysed for an association with toxicity whilst keeping the genotypes of the other polymorphisms constant. The test produces a p-value for each such test and then an overall p-value for that polymorphism which shows whether that polymorphism has a consistent association with toxicity regardless of background haplotype genotype. The first three panels show the effects of varying the 5' VNTR allele, 3'UTR allele and rs2612091 allele respectively. Only rs2612091 shows a significant effect overall. The lower two panels show two-polymorphism analyses in which rs2612091 is varied whilst 5'VNTR and 3'UTR alleles are held constant. Note that some rare haplotypes are not shown.

Table 8: Associations Between Selected Variants and Toxicity in the SCP Study.

Data are shown as for Table 6.

Table 9: Set Test Analyses of Capecitabine/5-FU Pathway Genes

Set tests used SNPs within 25 kb of each of the 25 capecitabine/5-FU pathway genes plus ENOSF1. Prior to analysis, the known DPYD 2846 and *2A variants and the newly identified DPYD rs12132152, DPYD rs7548189 and TYMS rs2612091, as well as anything in linkage disequilibrium of $r^2 > 0.1$ with these SNPs (including the TYMS 5'VNTR and 3'UTR polymorphisms), were removed. Tests were performed by individually testing the association of each SNP under an allelic model using logistic regression adjusted for age, treatment arm and gender, permuting the outcome data and re-testing 10,000 times, then comparing the observed distribution of p-values to those from randomly assigned toxicity data for each set (i.e. per gene or across all SNPs).

Table 10: Genotypes of QUASAR2 Individuals with Grade 4 Toxicity at Selected DPYD Variants.

For the toxicities, D=diarrhea, V=vomiting, H=HFS, N=neutropaenia, P=thrombocytpaenia, M=mucositis, S=stomatitis. The variants shown are (i) those identified by this study (rs12132152, rs12022243, rs2612091, DPYD A551T), (ii) DPYD alleles (2846 A>T and *2A) shown to be associated with 5-FU toxicity in the meta-analysis of Rosmarin et al (Rosmarin et al., *Journal of clinical oncology: official journal of the American Society of Clinical Oncology* (2014), in press, incorporated herein by reference) and (iii) potential DPYD toxicity alleles from Caudle et al (Caudle et al., *Clinical pharmacology and therapeutics* 94(6):640-5 (2013), incorporated herein by reference). Genotypes shown are major allele homozygote (0), heterozygote (1) and minor or variant allele homozygote (2). Blank cells denote missing data. The allele that provides a plausible explanation for the severe toxicity is shown. Note that *4 and *5 DPYD alleles are in complete linkage disequilibrium (D'=1.0) with 2A or 2846T>A.

Table 11: Associations Between DPYD Coding Regions Variants and Capecitabine Toxicity in QUASAR2.

Polymorphisms and rare variants present on the tagSNP or exome arrays are shown, together with summary statistics of association with toxicity in the meta-analysis of the two arms of QUASAR2. MAF=minor allele frequency.

TABLE 1

| Polymorphism | Toxicity | QUASAR2 Analyses | | | | | All Capecitabine Analyses | | | | | | |
|---|---|---|---|---|---|---|---|---|---|---|---|---|---|
| | | N | TAF | OR | 95% CI | p-value | S | N | OR | 95% CI | p-value | p-het | |
| *TYMS* 5'VNTR 2R/3R *2-repeat allele* | GLOBAL | 918 | 0.47 | 1.48 | 1.22-1.80 | 0.000079 | 5 | 1300 | 1.36 | 1.15-1.60 | 0.00028 | 0.17 | Meta |
| | DIARRHOEA | 918 | 0.47 | 1.29 | 0.96-1.74 | 0.093 | 5 | 1309 | 1.12 | 0.87-1.45 | 0.38 | 0.29 | |
| | HFS | 916 | 0.47 | 1.44 | 1.15-1.79 | 0.0013 | 5 | 1306 | 1.33 | 1.10-1.60 | 0.0029 | 0.23 | |
| *TYMS* 3'UTR 6bp ins-del *6bp-insertion allele* | GLOBAL | 474 | 0.69 | 1.67 | 1.23-2.22 | 0.00084 | 4 | 738 | 1.35 | 1.07-1.70 | 0.012 | 0.024 | Meta |
| | DIARRHOEA | 474 | 0.69 | 1.49 | 0.94-2.38 | 0.085 | 4 | 745 | 1.11 | 0.79-1.58 | 0.54 | 0.007 | |
| | HFS | 473 | 0.69 | 1.47 | 1.06-2.08 | 0.021 | 4 | 743 | 1.43 | 1.09-1.87 | 0.0091 | 0.34 | |
| 5'VNTR adjusted for 3'UTR | GLOBAL | 474 | 0.47 | 1.24 | 0.93-1.67 | 0.15 | 2 | 602 | 1.27 | 0.98-1.64 | 0.068 | — | Pooled |
| | DIARRHOEA | 474 | 0.47 | 1.08 | 0.70-1.67 | 0.72 | 2 | 602 | 1.11 | 0.76-1.61 | 0.59 | — | |
| | HFS | 474 | 0.47 | 1.26 | 0.91-1.75 | 0.17 | 2 | 602 | 1.20 | 0.90-1.58 | 0.21 | — | |
| 3'UTR adjusted for 5'VNTR | GLOBAL | 474 | 0.69 | 1.56 | 1.11-2.18 | 0.010 | 2 | 602 | 1.42 | 1.06-1.89 | 0.017 | — | Pooled |
| | DIARRHOEA | 474 | 0.69 | 1.47 | 0.88-2.45 | 0.14 | 2 | 602 | 1.19 | 0.78-1.81 | 0.43 | — | |
| | HFS | 474 | 0.69 | 1.37 | 0.94-1.98 | 0.10 | 2 | 602 | 1.40 | 1.02-1.93 | 0.038 | — | |
| *TYMS* score test *number of high-risk alleles* | GLOBAL | 474 | 0.58 | 1.38 | 1.16-1.64 | 0.00031 | 2 | 602 | 1.33 | 1.15-1.55 | 0.00018 | 0.46 | Meta |
| | DIARRHOEA | 474 | 0.58 | 1.24 | 0.96-1.61 | 0.096 | 2 | 602 | 1.14 | 0.92-1.42 | 0.24 | 0.20 | |
| | HFS | 474 | 0.58 | 1.31 | 1.08-1.59 | 0.0063 | 2 | 602 | 1.29 | 1.09-1.52 | 0.0030 | 0.73 | |
| *DPYD *2A exon skipping allele (A)* | GLOBAL | 905 | 0.004 | 2.78 | 0.62-12.5 | 0.18 | 2 | 1035 | 3.02 | 0.78-11.7 | 0.11 | 0.83 | Meta |
| | DIARRHOEA | 905 | 0.004 | 1.41 | 0.17-11.8 | 0.75 | 2 | 1035 | 3.14 | 0.71-13.8 | 0.13 | 0.18 | |
| | HFS | 903 | 0.004 | 2.67 | 0.59-12.0 | 0.20 | 2 | 1033 | 1.98 | 0.52-7.54 | 0.32 | 0.46 | |
| *DPYD 2846T > A A allele* | GLOBAL | 881 | 0.006 | 9.35 | 2.01-43.4 | 0.0043 | | | | | | | |
| | DIARRHOEA | 881 | 0.006 | 3.14 | 0.82-11.9 | 0.093 | | | | | | | |
| | HFS | 879 | 0.006 | 1.31 | 0.35-4.96 | 0.69 | | | | | | | |
| *DPYD combined allelic model 2846A or *2A A allele* | GLOBAL | 863 | 0.005 | 5.51 | 1.95-15.5 | 0.0013 | | | | | | | |
| | DIARRHOEA | 863 | 0.005 | 2.48 | 0.81-7.60 | 0.11 | | | | | | | |
| | HFS | 861 | 0.005 | 1.76 | 0.66-4.71 | 0.26 | | | | | | | |

Test alleles shown in italics.

TABLE 2

| | No. | % |
|---|---|---|
| Site | | |
| Colon | 930 | 89% |
| Rectum | 116 | 11% |
| Stage | | |
| II | 365 | 35% |
| III | 681 | 65% |
| Ethnicity | | |
| Caucasian | 1046 | 100% |
| Sex | | |
| Male | 593 | 57% |
| Female | 453 | 43% |
| Age, years | | |
| Median | 65 | |
| Minimum | 22 | |
| Maximum | 85 | |
| WHO performance status | | |
| 0-1 | 1046 | 100% |
| Treatment | | |
| Capecitabine (cap) | 496 | 47% |
| Cap + bevacizumab | 550 | 53% |
| Grade 3+ adverse events | | |
| Global | 353 | 34% |
| Diarrhoea | 109 | 10% |
| HFS | 247 | 24% |
| Mucositis | 11 | 1% |
| Stomatitis | 12 | 1% |
| Vomiting | 15 | 1% |
| Neutropaenia | 22 | 2% |
| Thrombocytopaenia | 4 | 0% |

TABLE 3

| Adverse Event | CTCAE grade | Patients |
|---|---|---|
| Global | 0 | 75 |
| | 1 | 241 |
| | 2 | 375 |
| | 3 | 334 |
| | 4 | 19 |
| | Unreported | 2 |
| Diarrhoea | 0 | 370 |
| | 1 | 388 |
| | 2 | 175 |
| | 3 | 99 |
| | 4 | 10 |
| | Unreported | 4 |
| Handfoot | 0 | 176 |
| | 1 | 287 |
| | 2 | 331 |
| | 3 | 246 |
| | 4 | 1 |
| | Unreported | 5 |
| Mucositis | 0 | 734 |
| | 1 | 248 |
| | 2 | 49 |
| | 3 | 11 |
| | 4 | 0 |
| | Unreported | 4 |
| Stomatitis | 0 | 718 |
| | 1 | 244 |
| | 2 | 67 |
| | 3 | 11 |
| | 4 | 1 |
| | Unreported | 5 |
| Vomiting | 0 | 817 |
| | 1 | 134 |
| | 2 | 74 |
| | 3 | 12 |
| | 4 | 3 |
| | Unreported | 6 |
| Neutropaenia | 0 | 921 |
| | 1 | 71 |
| | 2 | 28 |
| | 3 | 17 |
| | 4 | 5 |
| | Unreported | 4 |

TABLE 3-continued

| Adverse Event | CTCAE grade | Patients |
|---|---|---|
| Thrombocytopaenia | 0 | 961 |
| | 1 | 67 |
| | 2 | 9 |
| | 3 | 0 |
| | 4 | 4 |
| | Unreported | 5 |

TABLE 4

| Adverse Event | CTCAE grade | Highest CTCAE grade reported during treatment |
|---|---|---|
| Diarrhoea | 0 | 143 |
| | 1 | 23 |
| | 2 | 17 |
| | 3 | 32 |
| | 4 | 4 |
| | Unreported | 14 |
| Handfoot | 0 | 85 |
| | 1 | 28 |
| | 2 | 30 |
| | 3 | 86 |
| | 4 | 2 |
| | Unreported | 2 |

TABLE 5

| Gene Symbol | Gene Name | Location - Build 37 (coordinates do not include 25 kb flanking region) | Number of Test Panel SNPs |
|---|---|---|---|
| ABCB1 | ATP-binding cassette, sub-family B | chr7: 87132948-87342564 | 77 |
| ABCC3 | ATP-binding cassette, sub-family C, member 3 | chr17: 48712218-48769063 | 64 |
| ABCC4 | ATP-binding cassette, sub-family C, member 4 | chr13: 95672083-95953687 | 224 |
| ABCC5 | ATP-binding cassette, sub-family C, member 5 | chr3: 183637724-183735727 | 101 |
| ABCG2 | ATP-binding cassette, sub-family G, member 2 | chr4: 89011416-89152474 | 57 |
| CDA | cytidine deaminase | chr1: 20915444-20945400 | 26 |
| CES1 | carboxylesterase 1 isoform a precursor | chr16: 55836764-55867075 | 24 |
| CES2 | carboxylesterase 2 isoform a precursor | chr16: 66968347-66978994 | 59 |
| DPYD | dihydropyrimidine dehydrogenase | chr1: 97543300-98386615 | 239 |
| DPYS | dihydropyrimidinase | chr8: 105391652-105479277 | 69 |
| MTHFR | methylenetetrahydrofolate reductase | chr1: 11845787-11866115 | 38 |
| PPAT | phosphoribosyl pyrophosphate amidotransferase | chr4: 57259529-57301845 | 29 |
| RRM1 | ribonucleoside-diphosphate reductase subunit 1 | chr11: 4115924-4160106 | 29 |
| RRM2 | ribonucleoside-diphosphate reductase subunit 2 | chr2: 10262735-10270623 | 19 |
| SLC22A7 | solute carrier family 22 member 7 isoform b | chr6: 43265998-43273276 | 26 |
| SLC29A1 | equilibrative nucleoside transporter 1 | chr6: 44187242-44201888 | 26 |
| TK1 | thymidine kinase 1 | chr17: 76170160-76183285 | 35 |
| TYMP | thymidine phosphorylase | chr22: 50964182-50968258 | 92 |
| TYMS | thymidylate synthetase | chr18: 657604-673499 | 34 |
| UCK1 | uridine-cytidine kinase 1 isoform a | chr9: 134399191-134406655 | 43 |
| UCK2 | uridine-cytidine kinase 2 isoform a | chr1: 165796890-165877339 | 22 |
| UMPS | uridine monophosphate synthase | chr3: 124449213-124464040 | 34 |
| UPB1 | beta-ureidopropionase | chr22: 24890077-24922553 | 30 |
| UPP1 | uridine phosphorylase 1 | chr7: 48128355-48148330 | 16 |
| UPP2 | uridine phosphorylase 2 | chr2: 158851691-158992478 | 43 |

TABLE 6

| Gene | SNP b37 coordinate | Toxicity associated allele/ Other allele | TAF | N genotyped N imputed | Info Score $^A$ = Hap370 $^B$ = Hap610 $^C$ = Omni2.5 | Global Binary: 012v34 OR (95% CI) p-value | Global Quant: 01v2v34 OR (95% CI) p-value |
|---|---|---|---|---|---|---|---|
| DPYD | rs12132152 chr1: 97,523,004 | A/G | 0.031 | 456 484 | 0.993$^A$ | 3.83 (3.26-4.40) 4.31 × 10$^{-6}$ | 1.61 (1.41-1.82) 5.89 × 10$^{-6}$ |
| DPYD | rs76387818 chr1: 97,539,400 | A/G | 0.031 | 0 940 | 0.993$^A$ 0.999$^B$ 0.999$^C$ | 4.05 (3.47-4.62) 2.11 × 10$^{-6}$ | 1.66 (1.45-1.87) 1.93 × 10$^{-6}$ |
| DYPD | rs7548189 chr1: 97,867,713 | A/C | 0.196 | 940 0 | NA | 1.67 (1.43-1.91) 3.79 × 10$^{-5}$ | 1.23 (1.14-1.31) 6.82 × 10$^{-6}$ |
| DPYD | rs12022243 chr1: 97,862,780 | T/C | 0.196 | 0 940 | 0.996$^A$ 0.992$^B$ 0.998$^C$ | 1.69 (1.45-1.94) 2.55 × 10$^{-5}$ | 1.23 (1.14-1.32) 4.45 × 10$^{-6}$ |
| TYMS/ ENOSF1 | rs2612091 chr18: 683,607 | C/T | 0.532 | 940 0 | N/A | 1.59 (1.39-1.79) 5.28 × 10$^{-6}$ | 1.19 (0.77-0.91) 2.35 × 10$^{-6}$ |
| TYMS/ ENOSF1 | rs2741171 chr18: 700,687 | T/C | 0.534 | 0 940 | 0.960$^A$ 0.975$^B$ 0.990$^C$ | 1.6 (1.39-1.80) 6.64 × 10$^{-6}$ | 1.2 (1.13-1.28) 9.24 × 10$^{-7}$ |

TABLE 6-continued

| Gene | HFS Binary: 012v34 OR (95% CI) p-value | HFS Quant: 01v2v34 OR (95% CI) p-value | Diarrhoea Binary: 012v34 OR (95% CI) p-value | Diarrhoea Quant: 01v2v34 OR (95% CI) p-value | Other clinically actionable associations |
|---|---|---|---|---|---|
| DPYD | 6.12 (5.48-6.76) $3.29 \times 10^{-8}$ | 1.74 (1.53-1.95) $1.47 \times 10^{-7}$ | 0.44 (0-1.32) 0.065 | 0.85 (0.68-1.02) 0.068 | |
| DPYD | 6.44 (5.79-7.09) $1.75 \times 10^{-8}$ | 1.78 (1.57-1.99) $5.51 \times 10^{-8}$ | 0.44 (0-1.33) 0.071 | 0.86 (0.68-1.03) 0.083 | |
| DYPD | 1.42 (1.15-1.69) 0.011 | 1.16 (1.07-1.25) 0.0011 | 1.21 (0.84-1.58) 0.0015 | 1.18 (1.10-1.25) $1.54 \times 10^{-5}$ | Diarrhoea 01v234 1.76 (1.50-2.02) $1.72 \times 10^{-5}$ |
| DPYD | 1.43 (1.16-1.7) 0.0096 | 1.16 (1.07-1.25) $8.26 \times 10^{-4}$ | 1.79 (1.54-2.05) $9.86 \times 10^{-6}$ | 1.18 (1.11-1.26) $1.11 \times 10^{-5}$ | |
| TYMS/ ENOSF1 | 1.57 (0.45-0.83) $2.94 \times 10^{-6}$ | 1.21 (0.76-0.90) $3.67 \times 10^{-7}$ | 1.18 (0.55-1.15) 0.29 | 1.04 (0.90-1.03) 0.27 | HFS 01v234 1.57 (0.45-0.83) $2.94 \times 10^{-6}$ |
| TYMS/ ENOSF1 | 1.74 (1.51-1.97) $1.64 \times 10^{-6}$ | 1.23 (1.16-1.31) $3.10 \times 10^{-8}$ | 1.01 (0.70-1.32) 0.92 | 1.03 (0.97-1.09) 0.37 | HFS 01v234 1.61 (1.42-1.80) $1.44 \times 10^{-6}$ |

TABLE 7

| Test SNP | 5'VNTR 3'UTR rs2612091 | OR for effect of each test SNP allele on haplotypes | OR for pooled effect of both test SNP alleles | p-value |
|---|---|---|---|---|
| 5'VNTR (3 SNP model) | 2R/ins/G | 1 (ref) | 1 (ref) | 0.65 |
| | 3R/ins/G | 1.04 | | |
| | 2R/del/A | 0.89 | 0.83 | 0.34 |
| | 3R/del/A | 0.82 | | |
| | 2R/ins/A | 0.95 | 0.80 | 0.081 |
| | 3R/del/A | 0.77 | | |
| | overall | | | 0.17 |
| 3'UTR (3 SNP model) | 2R/ins/G | 1 (ref) | 1 (ref) | n/a |
| | 3R/ins/G | 1.04 | 1.04 | n/a |
| | 2R/del/A | 0.89 | 0.92 | 0.67 |
| | 2R/ins/A | 0.95 | | |
| | 3R/del/A | 0.82 | 0.80 | 0.33 |
| | 2R/ins/A | 0.77 | | |
| | overall | | | 0.61 |
| rs2612091 (3 SNP model) | 2R/ins/G | 1 (ref) | 1 (ref) | 0.66 |
| | 2R/ins/A | 0.95 | | |
| | 3R/ins/G | 1.04 | 0.84 | 0.00068 |
| | 3R/ins/A | 0.77 | | |
| | 2R/del/A | 0.89 | 0.88 | n/a |
| | 3R/del/A | 0.82 | 0.82 | n/a |
| | overall | | | 0.0021 |
| rs2612091 (2 SNP model) | 2R/G | 1 (ref) | 1 (ref) | 0.18 |
| | 2R/A | 0.92 | | |
| | 3R/G | 1.04 | 0.84 | 0.00051 |
| | 3R/A | 0.79 | | |
| | overall | | | 0.00053 |
| rs2612091 (2 SNP model) | ins/G | 1 (ref) | 1 (ref) | n/a |
| | ins/A | 0.80 | | |
| | del/A | 0.83 | 0.90 | n/a |
| | overall | | | 1.47E-06 |

TABLE 8

| Gene | SNP b37 coordinate | Association with selected phenotype |
|---|---|---|
| DPYD | rs12132152 chr1: 97523004 | 0.30 (0.10-0.86) 0.025 HFS 012v34 |
| DPYD | rs7548189 chr1: 97867713 | 1.66 (1.00-2.74) 0.048 HFS 012v34 0.78 (0.39-1.53) 0.46 Diarrhoea 012v34 |
| TYMS/ENOSF1 | rs2612091 chr18: 683607 | 1.64 (1.12-2.42) 0.012 HFS 012v34 |

TABLE 9

| SET | No. SNPs | Global 012v34 | Global 01v2v34 | HFS 012v34 | HFS 01v2v34 | Diarrhoea 012v34 | Diarrhoea 01v2v34 |
|---|---|---|---|---|---|---|---|
| ABCB1 | 77 | 0.29 | 1 | 1 | 1 | 1 | 1 |
| ABCC3 | 64 | 1 | 1 | 1 | 1 | 0.55 | 0.49 |
| ABCC4 | 221 | 0.86 | 0.87 | 1 | 1 | 0.91 | 0.75 |
| ABCC5 | 100 | 0.33 | 1 | 1 | 1 | 0.13 | 0.074 |
| ABCG2 | 57 | 0.093 | 1 | 0.37 | 0.60 | 1 | 1 |
| CDA | 25 | 1 | 0.24 | 0.38 | 0.20 | 1 | 0.40 |
| CES1 | 24 | 1 | 0.10 | 0.19 | 0.11 | 1 | 0.16 |
| CES2 | 59 | 0.18 | 0.28 | 0.0092 | 0.046 | 1 | 1 |
| DPYD | 189 | 0.31 | 0.040 | 0.52 | 0.52 | 0.53 | 0.20 |
| DPYS | 69 | 1 | 0.32 | 1 | 0.58 | 1 | 0.70 |

TABLE 9-continued

| SET | No. SNPs | Global 012v34 | Global 01v2v34 | HFS 012v34 | HFS 01v2v34 | Diarrhoea 012v34 | Diarrhoea 01v2v34 |
|---|---|---|---|---|---|---|---|
| ENOSF1 | 22 | 0.11 | 0.27 | 1 | 0.25 | 1 | 1 |
| MTHFR | 37 | 1 | 1 | 1 | 1 | 1 | 0.50 |
| PPAT | 29 | 1 | 1 | 1 | 1 | 1 | 0.10 |
| RRM1 | 29 | 1 | 1 | 0.17 | 1 | 1 | 1 |
| RRM2 | 19 | 1 | 1 | 1 | 1 | 1 | 1 |
| SLC22A7 | 26 | 1 | 1 | 1 | 1 | 0.014 | 0.22 |
| SLC29A1 | 26 | 1 | 1 | 1 | 1 | 1 | 1 |
| TK1 | 35 | 1 | 1 | 1 | 0.43 | 1 | 1 |
| TYMP | 92 | 1 | 0.24 | 0.035 | 0.025 | 0.055 | 0.029 |
| TYMS | 23 | 0.12 | 0.28 | 1 | 0.25 | 1 | 1 |
| UCK1 | 43 | 0.13 | 0.16 | 0.25 | 0.36 | 0.013 | 0.0038 |
| UCK2 | 21 | 1 | 1 | 1 | 1 | 0.063 | 0.31 |
| UMPS | 34 | 0.13 | 0.085 | 0.15 | 0.035 | 1 | 0.32 |
| UPB1 | 30 | 1 | 1 | 1 | 1 | 1 | 1 |
| UPP1 | 16 | 1 | 1 | 1 | 1 | 0.089 | 1 |
| UPP2 | 42 | 1 | 0.061 | 0.078 | 0.25 | 1 | 1 |
| As One Set* | 1393 | 0.72 | 0.36 | 0.67 | 0.55 | 0.10 | 0.12 |

TABLE 10

| Case | D | V | H | N | P | M | S | Possible explanation | 2846 | *2A | A551T | *13 |
|---|---|---|---|---|---|---|---|---|---|---|---|---|
| 1 | 4 | 0 | 2 | 0 | 0 | 0 | 0 |  | 0 | 0 | 0 | 0 |
| 2 | 4 | 0 | 0 | 0 | 0 | 0 | 0 |  | 0 | 0 | 0 | 0 |
| 3 | 0 | 4 | 0 | 0 | 0 | 0 | 0 |  | 0 | 0 | 0 | 0 |
| 4 | 4 | 2 | 2 | 0 | 0 | 0 | 0 |  | 0 | 0 | 0 | 0 |
| 5 | 4 | 0 | 0 | 0 | 0 | 0 | 1 | 2846T > A | 1 | 0 | 0 | 0 |
| 6 | 2 |  | 1 | 4 | 4 | 0 | 2 | 2846T > A | 1 | 0 | 0 | 0 |
| 7 | 3 | 0 | 2 | 4 | 4 | 3 | 3 | A551T | 0 | 0 | 1 | 0 |
| 8 | 3 | 1 | 3 | 4 | 2 | 3 | 3 |  | 0 | 0 | 0 | 0 |
| 9 | 4 | 0 | 2 | 0 | 0 | 1 | 0 |  | 0 | 0 | 0 | 0 |
| 10 | 4 | 1 | 3 | 0 | 0 | 1 | 0 |  | 0 | 0 | 0 | 0 |
| 11 | 4 | 2 | 1 | 1 | 0 | 0 | 0 |  | 0 | 0 | 0 |  |
| 12 | 0 | 0 | 3 | 4 | 4 | 3 | 3 | *2A | 0 | 1 | 0 | 0 |
| 13 | 4 | 0 | 1 | 0 | 1 | 1 | 1 |  | 0 | 0 | 0 | 0 |
| 14 | 0 | 4 | 3 | 0 | 1 | 0 | 0 |  | 0 | 0 | 0 | 0 |
| 15 | 4 | 0 | 1 | 0 | 0 | 1 | 1 |  | 0 | 0 | 0 | 0 |
| 16 | 4 | 0 | 2 | 0 | 0 | 0 | 0 |  | 0 | 0 | 0 | 0 |
| 17 | 1 | 0 | 4 | 0 | 0 | 0 | 0 |  | 0 |  | 0 | 0 |
| 18 | 2 | 4 | 3 | 0 | 0 | 0 | 1 |  | 0 | 0 | 0 | 0 |
| 19 | 3 | 0 | 2 | 4 | 4 | 0 | 4 | *13 | 0 | 0 | 0 | 1 |

| Case | *4 | *5 | *6 | *9A | M166V | K259E | rs12132152 | rs12022243 | rs2612091 |
|---|---|---|---|---|---|---|---|---|---|
| 1 | 0 |  | 0 | 0 | 0 | 0 | 0 | 0 | 2 |
| 2 | 0 | 0 | 0 | 0 | 0 | 0 | 0 | 1 | 2 |
| 3 | 1 | 1 | 0 | 0 | 0 | 0 | 0 | 1 | 1 |
| 4 | 0 | 0 | 0 | 2 | 1 | 0 | 0 | 0 | 0 |
| 5 | 1 | 1 | 0 | 0 | 0 | 0 | 0 | 0 | 0 |
| 6 | 1 | 0 | 0 | 0 | 0 | 0 | 0 | 2 | 1 |
| 7 | 0 | 0 | 0 | 0 | 0 | 0 | 0 | 1 | 2 |
| 8 | 0 | 2 | 0 | 0 | 0 | 0 | 0 | 1 | 2 |
| 9 | 1 | 0 | 0 | 0 | 0 | 0 | 0 | 1 | 2 |
| 10 | 0 | 0 | 0 | 0 | 0 | 0 | 0 | 1 | 2 |
| 11 | 0 | 1 | 0 | 0 | 0 |  | 0 | 1 | 2 |
| 12 | 0 | 0 | 0 | 1 | 1 | 0 | 0 | 0 | 1 |
| 13 | 0 | 1 | 0 | 0 | 0 | 0 | 0 | 1 | 1 |
| 14 | 0 | 0 | 0 | 1 | 1 | 0 | 0 | 1 | 2 |
| 15 | 0 | 1 | 0 | 0 | 0 | 0 | 0 | 0 | 1 |
| 16 | 0 | 0 | 0 | 0 | 0 | 0 | 0 | 1 | 1 |
| 17 | 0 | 0 | 0 | 0 | 0 | 0 | 0 | 1 | 0 |
| 18 | 0 | 1 | 0 | 0 | 0 | 0 | 0 | 0 | 0 |
| 19 | 0 |  | 0 |  |  | 0 |  |  |  |

TABLE 11

| variant ID | | | | | | Arm A | | | |
|---|---|---|---|---|---|---|---|---|---|
| Chr | Position | rs# | Classical ID | Nucleotide | Amino Acid | cases_AA | cases_AB | cases_BB | controls_AA |
| 1 | 97,547,947 | rs67376790 | 2846A > T | c.T2846A | p.D949V | 0 | 3 | 137 | 0 |
| 1 | 97,770,920 | rs1301160 | *6 | c.G2194A | p.V732I | 125 | 11 | 0 | 286 |
| 1 | 97,770,920 | rs1301160 | *6 | c.G2194A | p.V732I | 130 | 12 | 0 | 311 |
| 1 | 97,915,614 | rs3918290 | *2A | c.1905 + 1G > A | exon skipping | 140 | 2 | 0 | 330 |
| 1 | 97,981,143 | rs55886062 | *13 | c.T1879G | p.I360S | 141 | 1 | 0 | 330 |
| 1 | 97,981,395 | rs1801159 | *3 | c.A1627G | p.I343V | 89 | 33 | 12 | 198 |
| 1 | 97,981,421 | rs1801158 | *4 | c.G1601A | p.S534N | 135 | 7 | 0 | 317 |
| 1 | 98,059,419 | rs56018477 | | c.G1236A | p.E412E | 126 | 8 | 0 | 296 |
| 1 | 98,144,726 | rs45589337 | | c.A775G | p.K259E | 0 | 2 | 140 | 0 |
| 1 | 98,165,091 | rs2297595 | | c.A496G | p.M166V | 110 | 24 | 0 | 242 |
| 1 | 98,348,885 | rs1801265 | *9A | c.C85T | p.C29R | 8 | 40 | 86 | 18 |

| variant ID | Arm A | | Arm B | | | | | | Overall Analysis | |
|---|---|---|---|---|---|---|---|---|---|---|
| Chr | controls_AB | controls_BB | cases_AA | cases_AB | cases_BB | controls_AA | controls_AB | controls_BB | Meta Beta | Meta P |
| 1 | 2 | 328 | 0 | 3 | 190 | 0 | 0 | 340 | −2.284433 | 0.001 |
| 1 | 19 | 0 | 170 | 13 | 0 | 296 | 20 | 2 | 0.58056 | 0.8277 |
| 1 | 19 | 0 | 178 | 15 | 0 | 319 | 19 | 2 | 0.245417 | 0.3453 |
| 1 | 0 | 0 | 192 | 1 | 0 | 338 | 2 | 0 | 1.308234 | 0.1793 |
| 1 | 0 | 0 | 192 | 1 | 0 | 339 | 1 | 0 | 0.57783 | 0.6975 |
| 1 | 95 | 11 | 116 | 61 | 6 | 208 | 98 | 12 | 0.071863 | 0.3601 |
| 1 | 13 | 0 | 183 | 10 | 0 | 328 | 12 | 0 | 0.302948 | 0.3608 |
| 1 | 9 | 0 | 171 | 12 | 0 | 312 | 6 | 0 | 0.967362 | 0.0001 |
| 1 | 2 | 328 | 0 | 2 | 191 | 0 | 8 | 332 | 0.206601 | 0.7231 |
| 1 | 59 | 4 | 152 | 30 | 1 | 265 | 52 | 1 | −0.141077 | 0.4151 |
| 1 | 110 | 177 | 8 | 59 | 116 | 21 | 117 | 180 | 0.204385 | 0.0781 |

LIST OF FIGURES

FIG. 1: FU Metabolism Pathways

Capecitabine is an oral 5-FU pro-drug that is rationally designed so that concentrations of the cytotoxic metabolite FdUMP, FdUTP and FUTP are higher within malignant cells than within normal cells. Most of the drug activation occurs via the common pro-drug activation route (FIG. 1a). Additionally, 5-FU can be converted to the active compound via alternate activation routes in both colon tumour cells and cells from multiple other tissues (FIG. 1b). Toxicity may occur if non-target tissue is exposed to activated capecitabine/5-FU (e.g., FdUMP and FUTP), often when 5-FU exits target tissue and is subsequently activated. 5-FU released by cells into circulation may be quickly metabolised by the liver (FIG. 1c). Primary pathway is shown in solid lines; alternate pathways shown in dashed lines.

Figure 2:
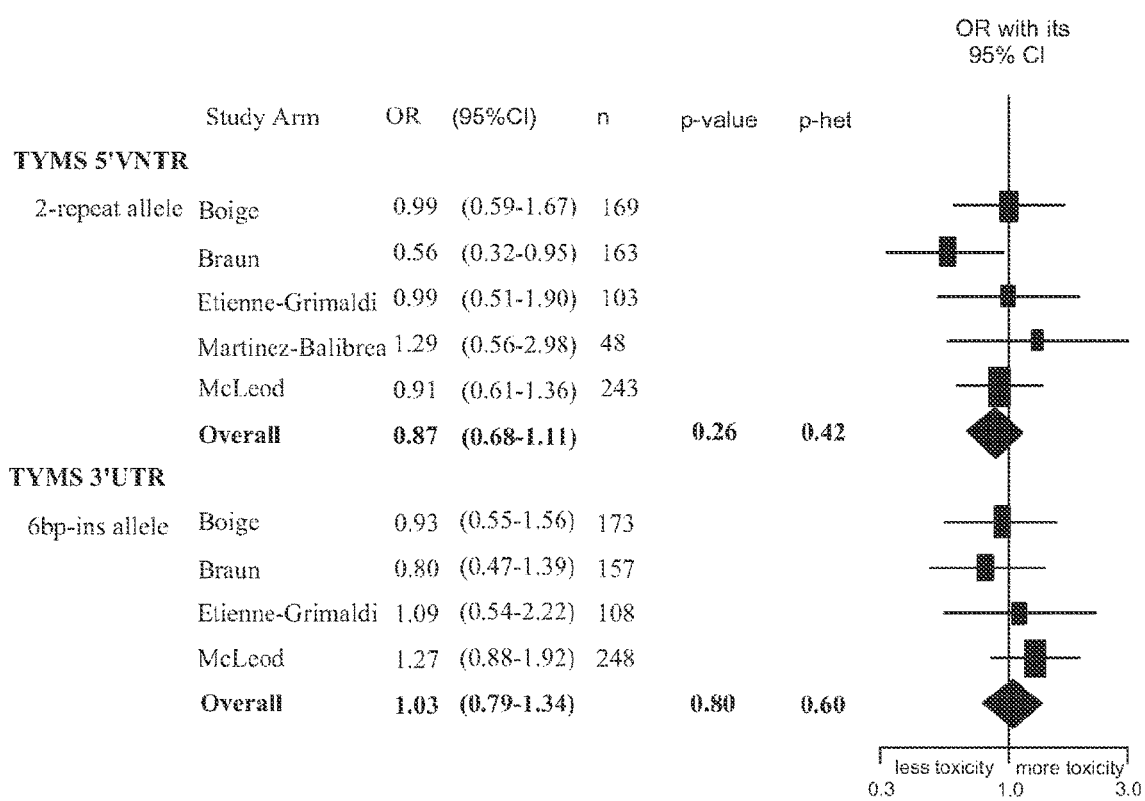

FIG. 2: Forest Plot of TYMS Polymorphisms Meta-Analysed in FOLFOX Patients (Allelic Model, Grade 0-2 v 3+ Global Toxicity)

Individual effects of two TYMS polymorphisms on global grade 3+ FU-related toxicity from FOLFOX treatment are shown, which are not significant (TYMS 5' 2R p=0.26; TYMS 3' 6 bp-ins allele p=0.8). Each trial is represented by a square, the centre of which denotes an odds ratio (OR) showing the increased proportion of patients experiencing high toxicity per test allele held (range 0-2 per patient, per polymorphism), while the horizontal lines show the 95% confidence intervals (CIs). The size of the square is directly proportional to the amount of information contributed by the trial. The diamonds represent overall ORs for the included studies, with the centre denoting the OR and the extremities the 95% CI. The fixed effect model was used. p-het=p-value for heterogeneity test, meta=meta-analysis.

Figure 3:
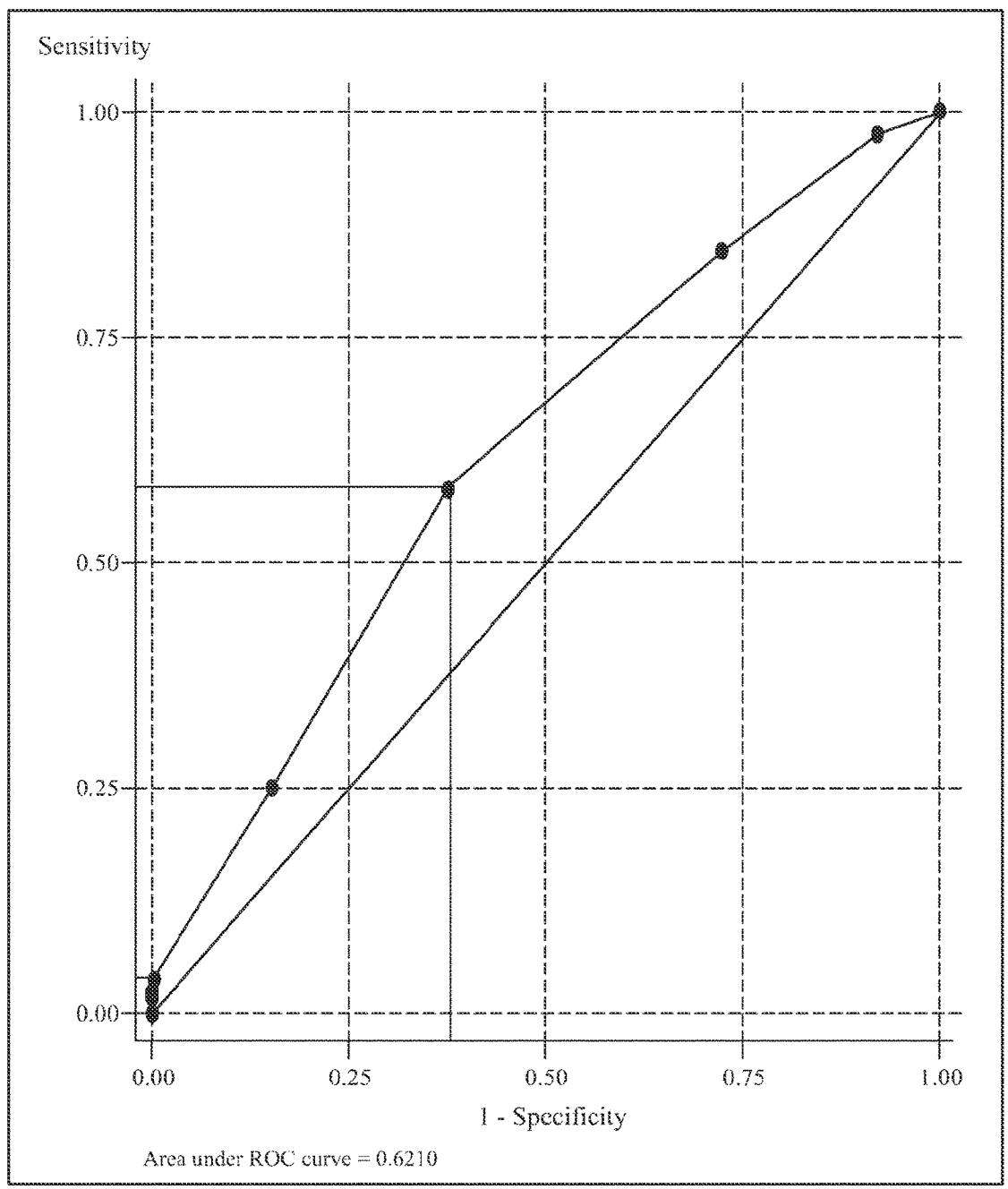

FIG. 3: FU Toxicity Receiver Operating Characteristics (ROC) Analysis of the TYMS 5'VNTR 2R/3R, TYMS 3'UTR 6 bp Ins-Del, DPYD 2846T>A and DPYD *2A Polymorphisms in QUASAR2 Capecitabine Patients Two sensitivity/specificity cut points are marked: that at the bottom-left of the plot corresponds to the maximum proportion of patients correctly classified, with sensitivity of 4%, specificity of 100% and a positive predictive value of 86%, largely due to rare DPYD variants; the other cut-point impacts more patients as a result of incorporating TYMS genotype and corresponds to sensitivity of 58%, specificity of 63% and a positive predictive value of 47%.

Figure 4A:
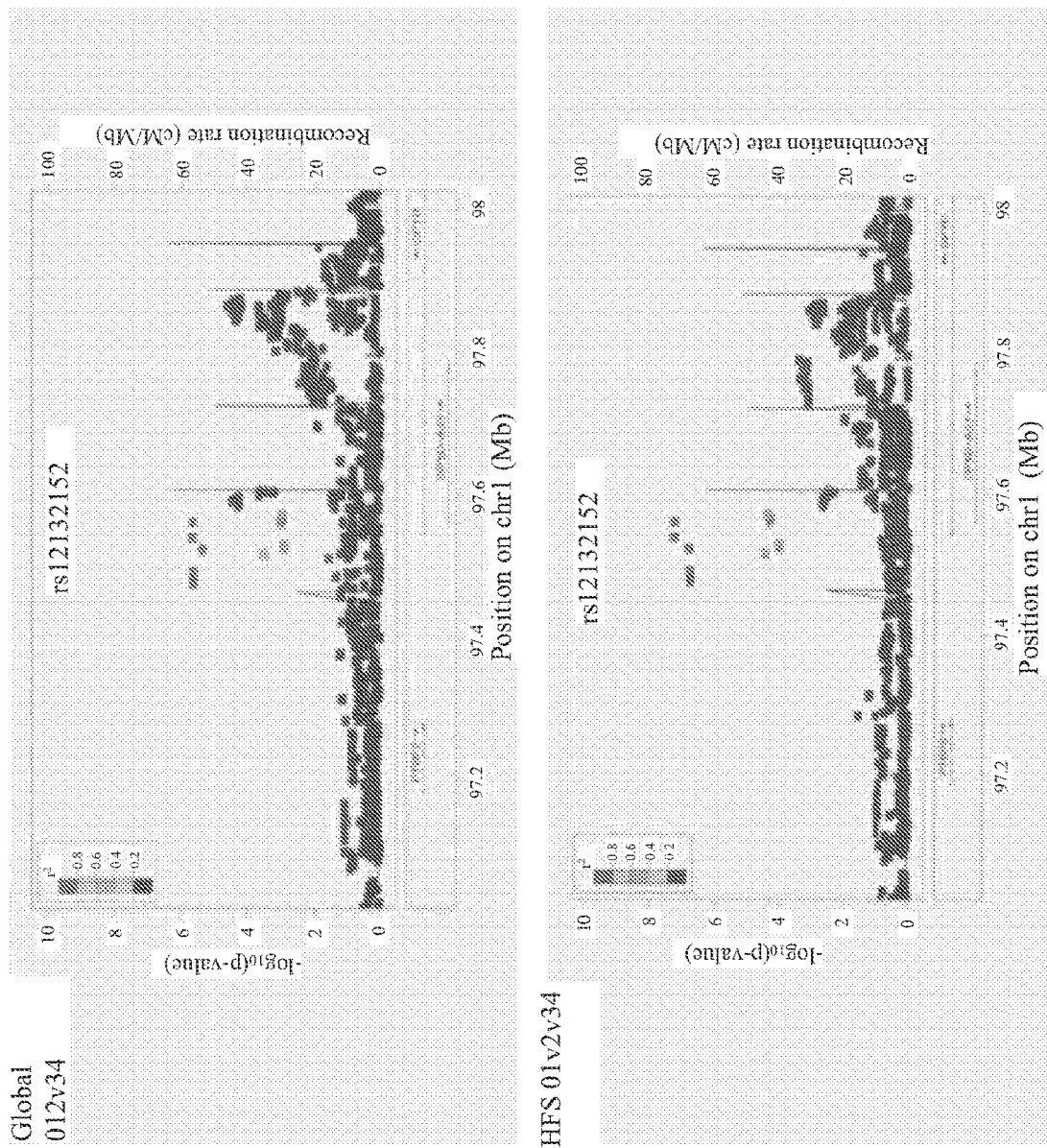
Figure 4A:
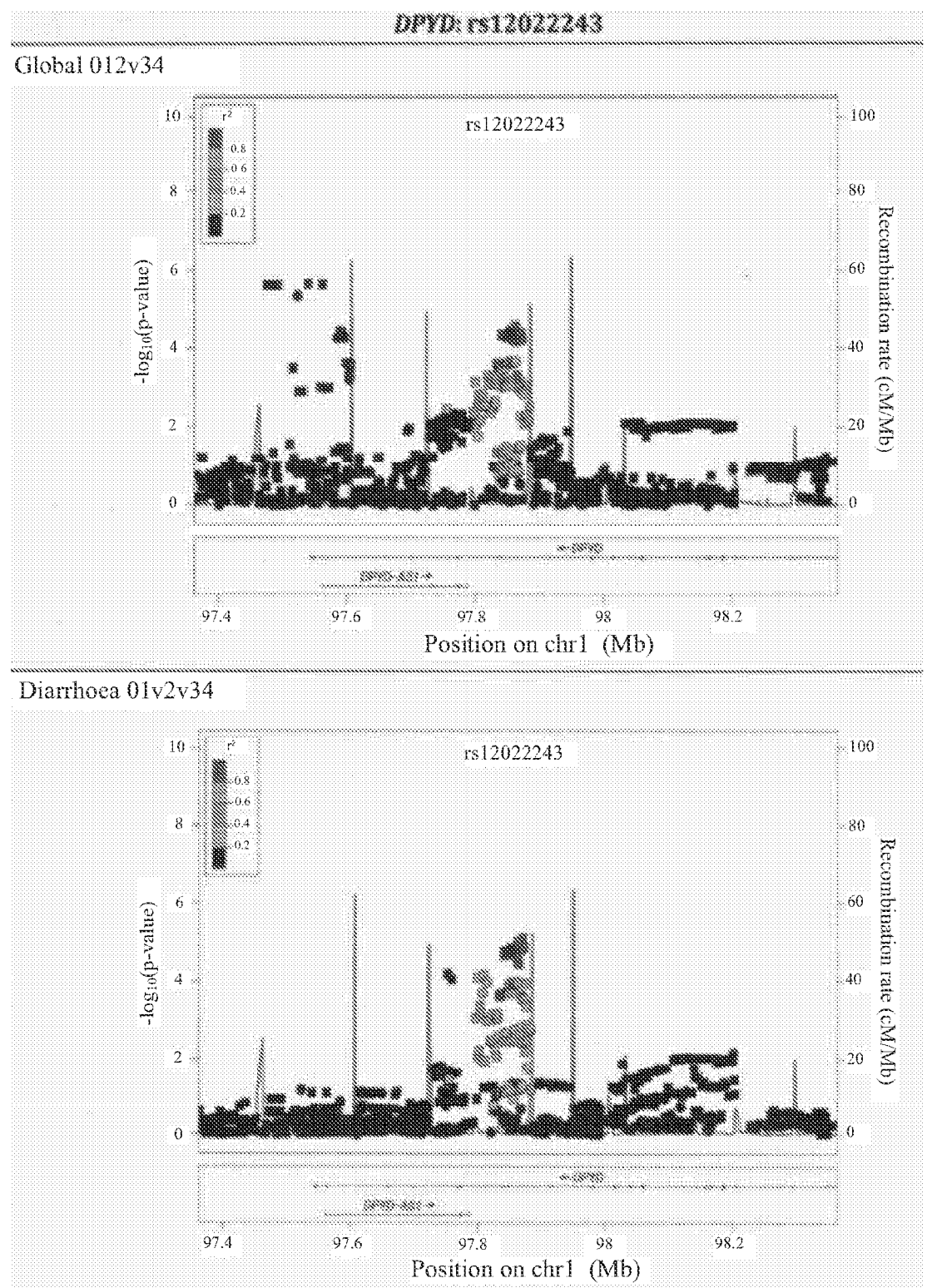

FIG. 4: Regional Plots of DPYD and TYMS for Associations with Capecitabine-Related Toxicity Associations with global grade 012v34 capecitabine-related toxicity and component toxicity phenotypes are shown for the regions flanking top tag SNPs in (a) DPYD and (b) TYMS/ENOSF1. The x-axis shows chromosome coordinate, whilst the y-axis shows the p-value for significance of the association, on a log scale. Circles represent SNPs included in our 1,456-SNP test panel, while squares represent imputed fine-map SNPs. Purple circles represent the tag SNPs of best association, and correlation with this SNP is shown by colour as indicated in each legend. For TYMS/ENOSF1, the most significant HFS 01v2v34 SNP (also the third most significant Global 012v34 SNP) is rs2741171. Plots made by LocusZoom.

Figure 5:
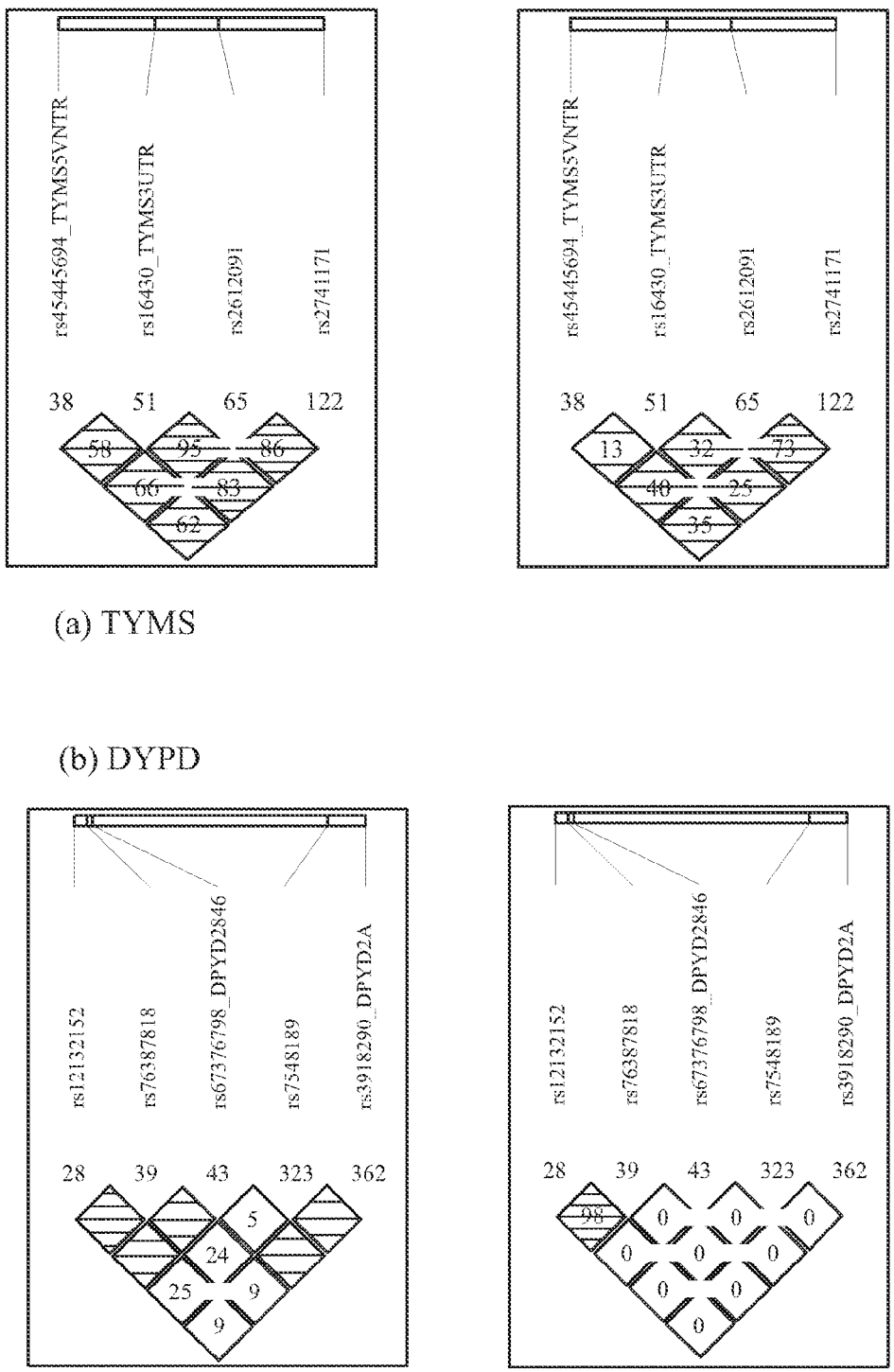

FIG. 5: LD Between Selected Variants Near (a) TYMS/ENOSF1 and (b) DYPD (Left=D'; Right=$R^2$).

Haplotype frequencies from Haploview EM algorithm are shown for TYMS.

Figure 6:
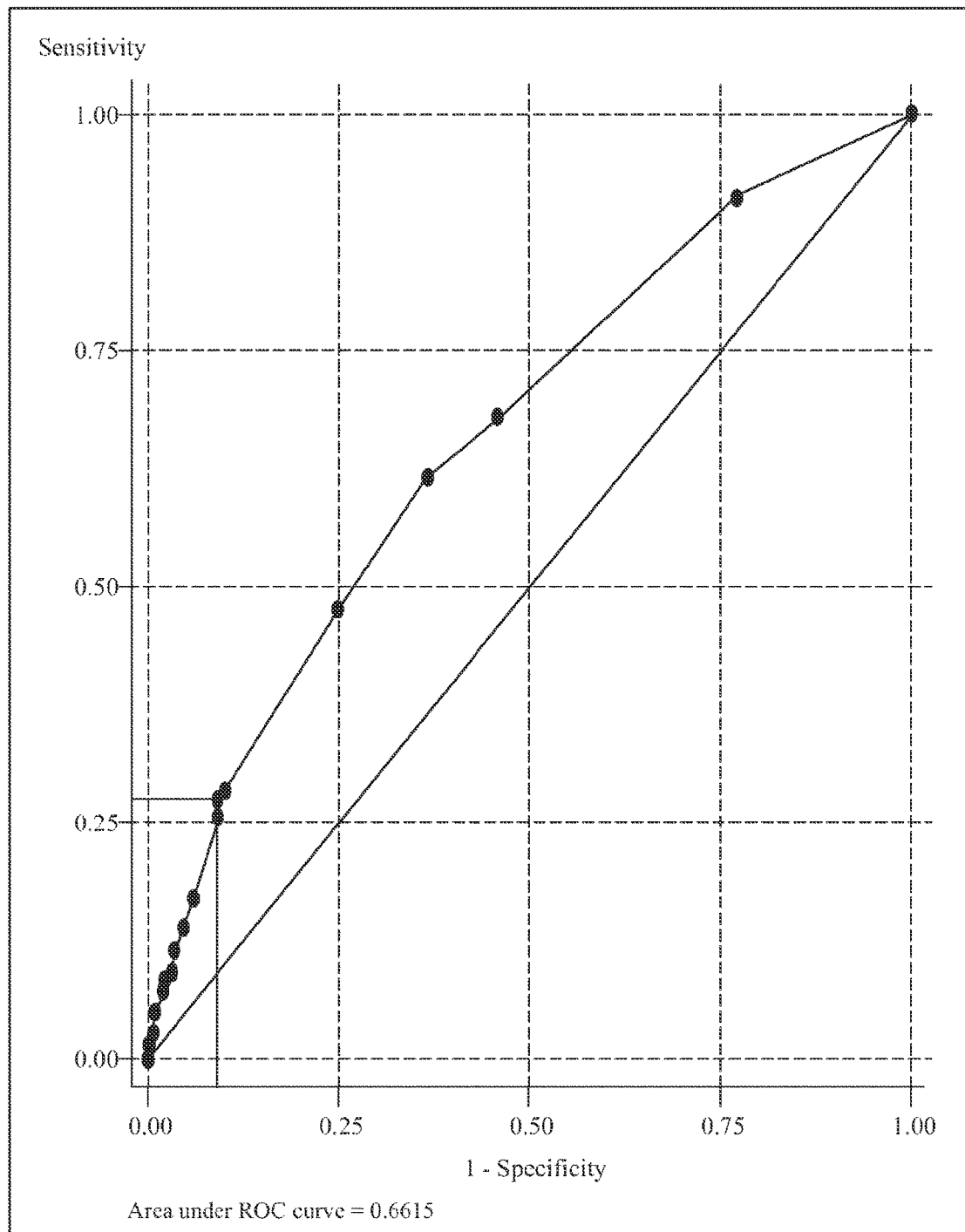

FIG. 6: Receiver Operating Characteristics (ROC) Analysis in QUASAR2 of Global Grade 012v34 Capecitabine-Related Toxicity Receiver operating characteristics (ROC) analysis of 938 capecitabine patients from the QUASAR2 trial, analysed for global capecitabine/5-FU-related grade 012v34 toxicity. Variants included in the model are the previously identified DPYD 2846T>A (rs67376798) and DPYD *2A (rs3918290) and the newly identified toxicity variants DPYD A551T, DPYD rs12132152, DPYD rs7548189 and TYMS rs2612091. Area under curve (AUC) is 0.66 (95% CI 0.63-0.70). Lines mark the cut-off at which the maximum proportion of patients are correctly classified (69%), at which sensitivity is 27% (95% CI 23-33%), specificity is 91% (95% CI 88-93%), PPV is 60% (95% CI 52%-68%), and NPV is 71% (95% CI 68%-74%).

EXAMPLES

The invention will be further clarified by the following examples, which are intended to be purely exemplary of the invention and are in no way limiting.

Example 1

As an overview, associations between candidate polymorphisms and capecitabine toxicity in patients from the trial described below ("QUASAR2") were examined. Meta-analysis was then performed combining these data with those from previously-published studies, both of capecitabine and other FU schedules. Finally, polymorphisms were identified that predict FU toxicity, and the sensitivity, specificity and predictive value of this test has been calculated.

a. Testing of Candidate FU-Pathway Toxicity Variants in the QUASAR2 Trial i. Patient and Study Characteristics The QUASAR2 study (http://www.octo-oxford.org.uk/alltrials/infollowup/q2.html; http://www.controlled-trials.com/ISRCTN45133151/) is a phase III randomised controlled trial of adjuvant capecitabine (Xeloda) (1250 mg/m2 twice daily d1-14 every 3 weeks, total of 8 cycles) +/−bevacizumab (7.5 mg/kg every three weeks) following resection of stage II/III CRC. Patients were entered into the study between July 2005 and December 2011 at 123 UK and 81 non-UK sites. Of 1119 patients with blood collected as of July 2010, 1046 were selected for study based on availability of clinical data and informed consent.

ii. Assessment of FU Toxicity

Adverse events were graded following each treatment cycle using the NCI Common Toxicity Criteria for Adverse Events (CTCAE) version 3.0. Common FU-related toxicities—diarrhea, nausea and vomiting, mucositis/stomatitis, neutropaenia, thrombocytopaenia, and HFS—were analysed individually and also in combination as "global" toxicity. Adverse events were categorised as low (CTCAE grade 0/1/2) and high (CTCAE grade 3/4/5 at any treatment cycle). Hypertension and proteinuria were clearly related to bevacizumab (~10-fold higher incidence) and were not included in the analysis. The incidence of FU-related toxicities did not differ materially between the two study arms and these were combined for analysis.

iii. Identification of Genetic Variants to Test for Associations with Capecitabine Toxicity In order to identify suitable FU pathway polymorphisms for testing in QUASAR2, a systematic review was performed of the literature. 139 searches in PubMed and Google Scholar were performed, first using the search terms "toxicity" in combination with "5-fluourouracil", "5-FU", or "capecitabine". The search was then repeated using identical search terms combined with the symbols of 8 genes identified in the initial search as having previous testing for an association with FU toxicity (24 separate searches).

From the resulting publications, both references and citing articles were reviewed, and any new genes and all polymorphisms were searched in combination with the initial search terms. Studies were considered for inclusion if they had: (i) used FU-based regimen(s); (ii) analysed genetic polymorphism(s) and/or rare variant(s) in relation to FU toxicity; and (iii) reported one or more of the 6 common FU toxicities listed above. A total of 49 publications met these criteria, which were subsequently further limited to those publications with: (i) sample size of 30 patients; (ii) Caucasian participants; and (iii) prospective design for collection of toxicity data.

This left 59 polymorphisms in 7 genes from a total of 28 studies, as disclosed in Boisdron-Celle M et al., *Cancer letters* 249(2): 271-82 (2007); Schwab M et al., *J Clin Oncol* 26(13): 2131-8 (2008); Afzal S et al., *Clin Cancer Res* 17(11): 3822-9 (2011); Lecomte T et al., *Clin Cancer Res* 10(17): 5880-8 (2004); Cohen V et al., *Clin Cancer Res* 9(5): 1611-5 (2003); Largillier R et al., *Clin Cancer Res* 12(18): 5496-502 (2006); Morel A et al., *Molecular cancer therapeutics* 5(11): 2895-904 (2006); Gross E et al., *PloS one* 3(12): e4003 (2008); Salgado J et al., *Oncology reports* 17(2): 325-8 (2007); Capitain O et al., *Pharmacogenomics J* 8(4): 256-67 (2008); Martinez-Balibrea E et al., *Eur J Cancer* 44(9): 1229-37 (2008); Ribelles N et al., *Current drug metabolism* 9(4): 336-43 (2008); Ruzzo A et al., *Pharmacogenomics J* 8(4): 278-88 (2008); Sharma R et al., *Clin Cancer Res* 14(3): 817-25 (2008); Afzal S et al., *Annals of oncology:official journal of the European Society for Medical Oncology/ESMO* 20(10): 1660-6 (2009); Braun M S et al., *J Clin Oncol* 27(33): 5519-28 (2009); Chua W et al., *Br J Cancer* 101(6): 998-1004 (2009); Derwinger K et al., *Clinical colorectal cancer* 8(1): 43-8 (2009); Gusella M et., *Br J Cancer* 100(10): 1549-57 (2009); Goekkurt E et al., *J Clin Oncol* 27(17): 2863-73 (2009); Boige V et al., *J Clin Oncol* 28(15): 2556-64 (2010); Etienne-Grimaldi M C et al., *British journal of clinical pharmacology* 69(1): 58-66 (2010); Martinez-Balibrea E et al., *Br J Cancer* 103(4): 581-9 (2010); McLeod H L et al., *J Clin Oncol* 28(20): 3227-33 (2010); Zarate R et al., *Br J Cancer* 102(6): 987-94 (2010); Caronia D et al., *Clin Cancer Res* 17(7): 2006-13 (2011); Martin M et al., *Clin Cancer Res* 17(7): 2006-13 (2011); Deenen M J et al., *Clin Cancer Res* 17(10): 3455-68 (2011); Glimelius B et al., *Pharmacogenomics J* 11(1): 61-71 (2011), all of which are incorporated herein by reference). Of these 59 variants, 4 were discarded since they could not be mapped unambiguously and a further 19 were invariant in all previous studies of FU toxicity, leaving 36 polymorphisms that remained for study.

iv. Genotyping of FU-Toxicity Variants in QUASAR2 Patients

940 QUASAR2 patients (439 capecitabine alone, 501 capecitabine+bevacizumab) of Caucasian ethnicity had toxicity data available. Patient genotypes for the 36 candidate polymorphisms were derived, and polymorphisms genotyped for at least 400 patients were included.

First, all patients had previously been genotyped using Illumina genome-wide single nucleotide polymorphism (SNP) panels (Human Hap 370, Human Hap 610 or Human Omni 2.5) and some polymorphism genotypes were extracted from these data. Standard quality control procedures for large association studies had previously been followed (Dunlop M G et al., *Nature genetics* 44(7): 770-6 (2012), incorporated herein by reference). Population stratification was examined by principal component analysis (PCA), and six cases that clustered with HapMap samples of known non-Caucasian ethnicity were removed. A further nine samples were excluded due to poor genotyping call rates (<95%).

Second, for variants absent from some or all of the SNP arrays, imputed genotypes were derived. The IMPUTE v2 program and the CEU participants of the 1000 genomes August 2009 data were used as a reference panel. Polymorphisms were included based on standard criteria (info scores >0.90 and missingness <0.10). A panel of individuals with whole-genome sequencing data was used to check the accuracy of imputation. Two variants were pruned due to very strong linkage disequilibrium (LD, r2>0.9) with other included variants.

Third, DPYD *2A, DPYD 2846T>A and CES2 823 were typed using the KASPar method of competitive allele-specific SNP genotyping (Cuppen E et al., CSH protocols 2007 pdb prot4841 (2007), incorporated herein by reference). TYMS 5'VNTR 2R/3R (Horie N et al., Cell structure and function 20(3): 191-7 (1995), incorporated herein by reference) and TYMS 3'UTR 6 bp ins-del (Dotor E et al., J Clin Oncol 24(10): 1603-11 (2006), incorporated herein by reference) were genotyped using known PCR-based methods.

Of the 21 included variants, 17 were genotyped in over 800 QUASAR2 patients and the remainder were typed in over 400 patients. For single SNP analyses in QUASAR2, all available genotypes were used in the analysis. For multivariate analyses, only the subset of samples genotyped for all variants under investigation was analysed.

It was found that 34% of QUASAR2 patients developed grade 3+ global toxicity (Table 2).

The most frequent specific grade 3+ toxicity was HFS (n=247), followed by diarrhea (n=109) and neutropaenia (n=22). Of the 21 genotyped and/or imputed FU-toxicity polymorphisms, three showed significant associations with global G3+ toxicity at q<0.05: TYMS 5'VNTR 2R (OR=1.48, 95% CI 1.22-1.80, p=0.000079); TYMS 3'UTR 6 bp ins (OR=1.67, 95% CI 1.23-2.22, p=0.00084); and DPYD 2846A (OR=9.35, 95% CI 2.01-43.4, p=0.0043) (Table 1).

Notably, no formally significant effect of 18 previously reported FU-variants on global or specific toxicities was found.

The 5'VNTR and 3'UTR TYMS polymorphisms have moderate linkage disequilibrium (LD) (r2=0.17, D'=0.64), and neither remained significantly associated with toxicity when adjusting for the other by logistic regression analysis (Table 1). These variants therefore are not independent markers.

In the absence of a well-defined genetic basis for the TYMS association signal, in order to capture the combined signal from the 5'VNTR and 3'UTR polymorphisms, a quantitative TYMS risk score (count 0-4 according to the number of high-risk alleles per patient) was tested. The score test predicted global FU toxicity ($OR_{per\ count}$=1.38, 95% CI 1.16-1.64, p=0.00031, logistic regression, Table 1; $OR_{score\ 3,4\ v\ score\ 0}$=3.70, 95% CI 1.35-10.1, p=0.0011). Based on pseudo-R2 statistics from logistic regression, the score test explained a greater proportion of variation than either individual TYMS variant.

The individual toxicities underlying the significant associations were also analysed. The TYMS polymorphisms (score test) appeared to have similar effects on HFS (OR=1.31, p=0.0063) and diarrhea (OR=1.24, p=0.096), but the former was more common and hence contributed more to the global measure and had greater statistical power in its analysis (Table 1). In contrast, the effects of DPYD 2846A appeared more marked for diarrhea (OR=3.14, p=0.093) than for HFS (OR=1.31, p=0.69) (Table 1).

b. Statistical Analysis

For each polymorphism, an allelic test of association with global G3+ toxicity was performed coupled with a logistic regression analysis adjusted for gender, age and arm, but inclusion of these variables made minimal difference to the results and these data are therefore not included.

For genes with consistent evidence of a toxicity association, additional investigations were performed. The TYMS 5'VNTR repeat haplotype was analysed by a binary model based on the total number of USF1/USF2 binding sites across both alleles (0-2 v 3-4) (Mandola M V et al., Cancer research 63(11): 2898-904 (2003), incorporated herein by reference), while the TYMS 5'VNTR and 3'UTR polymorphisms, which are in moderate linkage disequilibrium, were analysed in combination by logistic regression conditioned on study, haplotype analyses and a "score test" in which logistic regression was performed with toxicity for the number of TYMS risk alleles summed from the 3'UTR and 5'VNTR polymorphisms (0-4 alleles).

For DPYD, a combined assessment of rare variants with effects on enzyme function (DPYD *2A and 2846T>A) was undertaken as a group.

Receiver-operator characteristic (ROC) curves were generated by binary classification of patients to either G1/2 or G3/4/5 global toxicity and given a value based on $\Sigma\beta_i N_i$, where $\beta_i$ is the beta coefficient of the ith SNP significantly associated with global toxicity in a logistic regression model, and $N_i$ is the number of harmful alleles at that locus. Variants for inclusion were determined from the meta-analysis results. Area under the curve (AUC) was calculated and performance assessed at suitable cut-points based on the log likelihood ratio. Logistic regression was performed in PLINK. Haplotype construction was performed in Haploview.

c. Effect of FU-Toxicity Variants on Toxicity from Capecitabine Monotherapy

Fifteen FU-toxicity variants were analysed for associations with global capecitabine toxicity. The studies additional to QUASAR2 comprised a minority of the data, collectively contributing up to 382 patients.

An association was found between global toxicity and the TYMS 5'VNTR 2R allele (including QUASAR2: OR=1.36, 95% CI 1.15-1.60, p=0.00028; excluding QUASAR2: OR=1.09, 95% CI 0.80-1.48, p=0.27), but the variant was not significant alone when adjusting for 3'UTR 6 bp ins-del (Table 1).

The meta-analysis provided little support for the TYMS 3'UTR 6 bp ins-del association (including QUASAR2: OR=1.35, 95% CI 1.07-1.71, p=0.012; excluding QUASAR2: OR=0.94, 95% CI 0.64-1.38, p=0.74), but there was evidence of inter-study heterogeneity in the data (Phet=0.025, 12=68.0%), originating from one relatively small study of 80 patients. The TYMS score test meta-analysis, which utilised data from the two largest studies, continued to show a highly significant association (including QUASAR2: OR=1.33, 95% CI 1.15-1.55, p=0.00018, excluding QUASAR2: OR=1.21, 95% CI 0.89-1.63, p=0.22).

The association between toxicity and DPYD 2846T>A is also significant, but this variant was only tested in QUASAR2 (see above).

i. Data Overview

Four specific germline TYMS and DPYD variants have been found to predict capecitabine toxicity; TYMS 5'VNTR 2R/3R, TYMS 3'UTR 6 bp ins-del, DPYD 2846T>A, and DPYD *2A. The analysis suggests that the polymorphisms may also be useful in predicting toxicity in other FU monotherapy regimens, but these regimens are used uncommonly.

It is not clear whether the DPYD *2A and DPYD 2846T>A polymorphisms analysed are also associated with global or any specific toxicity in the combination therapy regimens (FOLFOX, CAPDX, FOLFIRI, IFL, FURI). FIG. 2 shows the results from meta-analysis of the two main TYMS polymorphisms in studies using FOLFOX, the largest combination therapy data set.

Despite some previous suggestions to the contrary in the cited literature, evidence of any association with toxicity was unconvincing for the remaining polymorphisms. Some of these (DPYD 1627A>G, DPYD 85T>C, DPYD 496A>G, TYMS 5'VNTR G>C, MTHFR 677C>T, MTHFR 1298A>C, CDA-451C>T, CES2 823C>G, and the TYMP polymorphisms) are common (MAF>8%) and all but modest effects could be excluded with confidence where sample sizes were relatively large. Power to detect an association for these SNPs was approximately 75-100% assuming an odds ratio of 1.5 per allele. For other polymorphisms (for example, DPYD 1601G>A, DPYD 1236G>A, DPYD 2194G>A, CDA 943insC, and most CES2 polymorphisms), minor allele frequencies were low or sample sizes small, leading to sub-optimal power (approximately 20-40%) to detect an association. The case for these as markers of toxicity remains unproven.

d. Combined Analysis of Rare DPYD Alleles with Evidence of Effects on Enzyme Function For alleles within a single gene that have equivalent functional effects causally related to toxicity, it is justifiable to combine these into one functional class for predictive testing. For DPYD, some rare variants have been proposed to cause DPYD Deficiency Syndrome (OMIM #274270) (van Kuilenburg A B et al., *The Biochemical journal* 364(Pt 1): 157-63 (2002); Van Kuilenburg A B et al., *Human genetics* 104(1): 1-9 (1999), both incorporated herein by reference). Of these, a few have been shown to reduce DPYD activity in vitro (Offer S M et al., *Cancer research* (2013), incorporated herein by reference), whilst others have lesser functional evidence from in vivo reports (Seck K et al., *Clin Cancer Res* 11(16): 5886-92 (2005); van Kuilenburg A B et al., *Clin Cancer Res* 6(12): 4705-12 (2000), both incorporated herein by reference). Among variants found in the patient sets, good published evidence was found of functionality for DPYD 2846A and *2A (van Kuilenburg A B et al., *The Biochemical journal* 364(Pt 1): 157-63 (2002); Van Kuilenburg A B et al., *Human genetics* 104(1): 1-9 (1999), both incorporated herein by reference), but not for *9A (85T>C) or Ile370Val (1108A>G), despite these having previously been reported as causing DPYD Deficiency.

Therefore an analysis of DPYD 2846T>A and *2A rare alleles was performed as a group (either variant versus no variant) in a "group test". A formally significant association with global toxicity for capecitabine was found (indicating that the combined associated risk is relatively high) (OR=5.51, 95% CI 1.95-15.51, p=0.0013; data from QUASAR2 alone, Table 1), and nominally-significant associations in the analyses for infusional (p=0.042) and bolus (p=0.0068) monotherapies. All of these associations were stronger than when either of the variants was considered alone.

e. Performance of Panels of Polymorphisms for Predicting FU Toxicity

There are currently three commercially-available kits for predicting FU toxicity. These kits contain a total of 17 polymorphisms that fall into 3 categories: (i) evidence of toxicity prediction in the present analysis (n=4); (ii) present in the present analysis but without good evidence of predictive ability (n=5); or (iii) absent from the present analysis (n=8). Of the variants in category (iii), 5 are rare DPYD variants with evidence of harmful effects on enzyme function (1679(*13), 1897(*3), 295-298del(*7), 703(*8) and 2983(*10)) (van Kuilenburg A B et al., *The Biochemical journal* 364(Pt 1): 157-63 (2002); Van Kuilenburg A B et al., *Human genetics* 104(1): 1-9 (1999), both incorporated herein by reference).

In the QUASAR2 capecitabine patients, the sensitivity and specificity of global toxicity prediction was determined by each kit, following the instructions as closely as possible and using a binary classification of toxicity (no/low risk versus moderate/intermediate/high risk). Owing to the inclusion of common polymorphisms, two kits classified almost all patients as having a high risk of toxicity, with false positives greatly outnumbering true positives. The remaining kit provided a sensitivity of no more than 29%.

It was assessed whether the performance of the kits could be improved using the developed DPYD combined rare functional alleles test and the TYMS score test (as described in Example 1(b)). Independent effect size estimates were used (using raw data from Caronia D et al., *Clin Cancer Res* 17(7): 2006-13 (2011)) and applied to QUASAR2 in a logistic regression model. AUC was 0.62 (95% CI 0.57-0.67).

At a ln(p/1-p) cut-off of 0.698—at which the maximum proportion of cases (64%) was correctly classified—sensitivity was 3.8%, specificity 99.6%, PPV 86% (95% CI 42-99%), and NPV 64% (95% CI 59-69%), mostly reflecting just rare DPYD variants. At a ln(p/1-p)cut-off of 0.248, sensitivity was 58% and specificity 63%, with 61% patients correctly classified (FIG. 3); the PPV was 47% (95% CI 40-55%) and NPV 72% (95% CI 66%-77%).

Accordingly, screening for the presence of the two TYMS variants and functional DPYD variants is predictive of FU toxicity. However there remains a need to identify and characterise additional FU toxicity variants in order to provide improved tests with greater predictive power for use in clinical practice. Such improved genetic tests would provide the ability to closely monitor patients who are at increased risk of toxicity or to increase FU dosage in those who are at low risk of toxicity.

Example 2

Further analysis of patients from the QUASAR2 trial has led to identification of rare genetic variants in 25 capecitabine/5-FU pathway genes and subsequent exon sequencing of DPYD and TYMS. Further, the sensitivity, specificity and predictive value of this test has been calculated.

a. Assessment of FU Toxicity in the QUASAR2 Trial i. Patient and Study Characteristics The QUASAR2 study was used as described in Example 1(a)(i). Of 1,119 patients with blood collected as of July 2010, 1,046 were selected for genetic study based on completeness of clinical data and informed consent. Patient characteristics are shown in Table 2.

ii. Assessment of FU Toxicity

Toxicity phenotype data were collected as part of QUASAR2 according the NCI Common Toxicity Criteria for Adverse Events (CTCAE) version 3.0. Maximum toxicity (0-4) at any treatment cycle was derived for each of the following individual FU-related toxicities: diarrhea, nausea and vomiting, mucositis/stomatitis, neutropaenia, thrombocytopaenia and HFS. A global measure of toxicity was derived, defined as the maximum individual toxicity score measured for each patient. Global and individual toxicities were analysed using two approaches: (i) a binary classification into low toxicity (grade 0-2) versus high (dose-limiting) toxicity (grade 3-4); and (ii) a quantitative measure of toxicity. In the latter, if <100 patients experienced a particular grade of toxicity, these patients were combined into a single bin with an adjacent grade. Specifically, grades 01v2v34 for global, diarrhea and HFS and 0v1234 for the other, rarer toxicity phenotypes were analysed. Toxicity data by grade are shown in Table 3.

Grade 3+ global toxicity was observed in 34% of these patients, with severe diarrhea in 10% and HFS in 24%. Severe toxicity was less common for the other phenotypes, although five patients experienced grade 4 neutropaenia.

b. Identification of Genetic Variants to Test for Associations with Capecitabine Toxicity i. Validation Patient Sets Two additional data sets were used for validation of toxicity associations. The Spanish Capecitabine Pharmacogenetic (SCP) Study consisted of 233 colorectal and breast cancer patients prospectively recruited through several oncology units in Spain and treated with one of two capecitabine monotherapy regimens (standard: 1250 mg/m$^2$ twice daily d1-14 every 3 weeks; continuous: 800 mg/m$^2$ orally every 12 hours daily). HFS and diarrhea data Table 4 were collected according to CTCAEv3.0.

The EPICOLON study has been described previously (Abuli A, et al. *Carcinogenesis* (Epub ahead of print) (2013), incorporated herein by reference). The 85 EPICOLON cases included in this analysis were those receiving capecitabine monotherapy. Only diarrhea toxicity data were available from these cases.

ii. Genotype Data

For QUASAR2, genotype data from patients' constitutional DNA samples were available from single nucleotide polymorphisms (SNPs) and rare, coding genetic variants that had been analysed using standard methods and subjected to standard quality control procedures to eliminate poorly-performing samples and polymorphisms (Dunlop M G et al., *Nat Genet.* 44(7): 770-776 (2012), incorporated herein by reference). Only individuals clustering with the CEPH CEU panel on principal component analysis were included in the study. For the SNP arrays, based on haplotype-tagging single nucleotide polymorphisms (SNPs), data were available for 940 patients (484 from Illumina Hap300 or Hap370CNV, 364 from Hap610 and 92 from Omni2.5). For the exome arrays, designed to capture uncommon protein-coding variation, data were available for 968 patients genotyped on the Illumina HumanExome12v1_A or -12v1-1_A array. Base calling for all platforms was performed using Illumina Genome Studio and, for exome arrays, additionally by Z-Caller (Goldstein J I et al., *Bioinformatics* 28(19): 2543-2545 (2012), incorporated herein by reference), applying a z-score of 7 based on the concordance of calls with Illumina Genome Studio for common variants (99.3%). Some polymorphisms were present on both the SNP array and exome array and the genotype concordance for these variants was 99%.

From 25 candidate capecitabine/5-FU pathway genes Table 5, variants were identified that were present on one or more of the Hap300/370, Hap610 or exome arrays and that lay within 25 kb of the coding region. Imputation was used to obtain missing genotypes arising from differences in array content: haplotypes were phased using SHAPEITv2 (Delaneau O et al., *Nat Methods* 10(1): 5-6 (2013), incorporated herein by reference) and imputation performed using IMPUTEv2 (Howie B et al., *Nat Genet.* 44(8): 955-959 (2012), incorporated herein by reference), employing a 250 kb buffer region and the 1000 genomes 2012 release (all ethnicities) as a reference panel. Only SNPs with an IMPUTEv2 info score of at least 0.95 on each array individually were taken into further analysis by SNPTESTv2 (Marchini J et al., *Nat Genet* 39(7): 906-913 (2007), incorporated herein by reference). Further exclusion criteria were a SNPTEST info score below 0.95 on the pooled score from the three SNP arrays, a minor allele frequency below 0.01 and a Hardy-Weinberg equilibrium p-value below 0.0001. Genotyping and imputation provided a total of 1,456 genetic variants for analysis.

For the SCP study, genotyping was performed by the Illumina Hap610 platform, with quality control measures and statistical analysis with SNPTESTv2 as described above for QUASAR2. For EPICOLON, genotyping was performed using KASPar on genome-amplified DNA.

Further genotyping was performed for the TYMS 5'VNTR and 3'UTR variants by previously-described methods (Horie N et al., *Cell Struct Funct.* 20(3): 191-197 (1995); Dotor E et al., *J Clin Oncol* 24(10): 1603-1611 (2006), both incorporated herein by reference). Additional genotyping of the DPYD 2846T>A and DPYD *2A variants was performed by KASPar (Cuppen E CSH Protoc 2007: pdb prot4841 (2007), incorporated herein by reference) for the small number of patients not genotyped using the exome arrays.

For loci at which significant associations between genetic variants and toxicity were detected, fine mapping studies were performed using the methods above to impute all SNPs in a 1.5 Mb flanking region, in order to refine the association signal.

iii. Sequencing

Sequencing of the coding regions of DPYD and TYMS was performed by Roche/454 Titanium GS FLX technology according to the specified amplicon sequencing protocol (see http://454.com/downloads/my454/documentation/gs-junior/method-manuals/GSJunior_AmpliconLibraryPrep-RevJune2010.pdf).

Specifically, 100 patients with the highest levels of 5-FU-related toxicity ("HiTox"), specifically grade 3 or grade 4 diarrhea in the first 4 cycles of treatment and or other grade 3/4 toxicities in the first 4 cycles of treatment were selected. 100 patients with no adverse toxicity events during the entire duration of treatment ("LoTox") were also selected. Using DNA from peripheral blood, PCR primers and reactions were designed to cover all 23 DPYD exons (27 amplicons; 4,784 bp) and 7 TYMS exons (9 amplicons; 2,276 bp).

Constitutional DNA samples from each patient were quantitated using PicoGreen, diluted to equal measured concentrations and formed into 10 pools of 20 patients each. Pools were then PCR-amplified for each of the 36 amplicons. Missing or undesired amplicons were identified by an Agilent High Sensitivity DNA Kit. Successful amplicons were quantified by PicoGreen according to the 454 protocol, equalised in concentration and formed into one 100-patient HiTox pool and one 100-patient LoTox pool for sequencing. The aim was to achieve a minimum read depth of 3,000 per target locus per pool (that is about 30× coverage per patient).

The missense DPYD variant p.Ala551Thr (A551T) was identified in the HiTox pool. The DNA for each individual comprising the pool was Sanger-sequenced to identify those carrying this variant. Only one heterozygous individual was found.

For analysis of the whole sample set, KASPar (http://cshprotocols.cshlp.org/content/2007/9/pdb.prot4841.abstract) allele specific single-nucleotide variant primers were designed to detect A551T and included three duplicates of the known variant sample in each run to facilitate genotype clustering. All samples that did not cluster with the A allele homozygotes were subsequently examined by bidirectional Sanger sequencing.

iv. Statistical and Computational Analysis

For each of the 1,456 SNP and exome array variants, primary analysis tested associations between global (any 5-FU-related) dose-limiting (grade 0l2v34) toxicity and genotype. Frequentist tests under a missing data linear or logistic regression model were implemented using SNPTESTv2. Samples were stratified by QUASAR2 treatment with age and gender as covariates. Meta-analysis of the two arms (439 patients in arm A (capecitabine) and 501 patients in arm B (capecitabine+bevacizumab) of QUASAR2 was performed using GWAMA (http://www.well.ox-.ac.uk/gwama/download.shtml), including tests of inter-arm heterogeneity. Bonferroni-corrected p-value threshold of $3.43 \times 10^{-5}$ (=0.05/1456) was used to indicate a significant association for the primary analysis of (binary) global dose-limiting toxicity.

For selected SNPs with association signals that reached or approached formal significance, additional SNPs were imputed within 1.5 Mb flanking regions. Association tests were performed for global and specific toxicities using the global grade 0l2v34 measure. Since the genotyped and imputed SNPs were non-independent, associations with imputed SNPs were declared significant using the same threshold of $p=3.43 \times 10^{-5}$. For any region within which one or more SNPs achieved significant associations with global toxicity, the underlying individual toxicities were investigated at the most strongly associated SNPs using both quantitative measures and clinically-actionable cut-offs for dose delay or reduction in QUASAR2 (generally grade 0l2v34, except for grade 0lv234 for diarrhea).

Logistic regression analysis in R was used to test for independent effects of variants within a region. The best-fitting model was determined as that which minimised the Akaike information criterion (AIC) subject to a variant showing an association at p=0.05. Haplotype analyses were performed using the "—hap-logistic" and "—independent-effect" commands in PLINK (Purcell S et al., *American Journal of Human Genetics* 81(3): 559-75 (2007) incorporated herein by reference). Tests to examine multiple genetic variants were performed in PLINK. Receiver operator characteristic (ROC) analysis was performed in Stata using a binary classification of patients to either grade 0/1/2 or grade 3/4 global toxicity, using a genetic score given for each individual by $\Sigma \beta_i N_i$, where $\beta_i$ is the beta coefficient of the ith SNP significantly associated with global toxicity in a logistic regression model, and Ni is the number of harmful alleles carried by that individual at that locus.

Functional annotation of variants was performed with ANNOVAR. mRNA expression data were obtained from Genevar (Yang T P et al., *Bioinformatics* 26(19): 2474-2476 (2010), incorporated herein by reference) and from The Cancer Genome Atlas (TCGA), which were analysed according to the methods of Qiyuan et al (Li Q Y et al., *Cell* 152(3): 633-641 (2013), incorporated herein by reference).

For sequencing data, putative associations with toxicity were determined according to the estimated number of variant and wildtype reads present in the HiTox and LoTox pools (Pearson's Chi Squared or Fisher's exact test).

c. New Associations with Toxicity at the DPYD Locus

Using a Bonferroni-corrected p-value threshold of $3.43 \times 10^{-5}$ for the primary analysis of global dose-limiting toxicity (grade 0l2v34), analysis was carried out to search for associations between the genetic variants and capecitabine toxicity. These analyses identified two novel DPYD toxicity SNPs.

It was found that the A-allele (freq.=0.03) of SNP rs12132152 was associated with global capecitabine toxicity ($OR_{globalbinary}$=3.83, p=4.31×10$^{-6}$, Table 6).

rs12132152 is an intergenic SNP variant 22 kb downstream of DPYD (chr1:97,523,004, b37). Upon imputation of variants in the region flanking this tag SNP, SNPs were identified with marginally more significant associations, notably rs76387818 (chr1:97,539,400, $OR_{globalbinary}$=4.05, p=2.11×10$^{-6}$, $r^2_{tag}$=0.98; Table 6; FIG. 4a). Similar results were obtained when the quantitative measure of global toxicity was used (Table 6).

The individual phenotypes comprising the global toxicity measure were investigated. rs12132152 and rs76387818 were strongly associated with HFS under both quantitative and binary models (for rs76387818, $OR_{hfsquant}$=1.78, p=5.51×10$^{-8}$, $OR_{hfsbinary}$=6.44, p=1.75×10$^{-8}$), but not with any other individual toxicity.

The in silico possible functional mechanisms underlying the rs12132152/rs76387818 association were further investigated.

The ENCODE data (http://genome.ucsc.edu/ENCODE/) for the region containing rs12132152 and seven strongly correlated SNPs (FIG. 4a: approximately chr1:97,475,000-97,562,000, b37) were examined. FAIRE and histone K4 methylation data suggested that this is a region of open chromatin and one correlated SNP in particular, rs12123160, lies at a methylated CpG. Although no suitable data from normal liver were available, genotypes at rs12132152 and correlated SNPs were found not to be associated with DPYD expression in adipose tissue, lymphoblastoid cells or skin (Genevar database, p>0.13) (Nica A C et al., *Plos Genetics* 7(2) (2011), incorporated herein by reference) or in colon tissue (The Cancer Genome Atlas (TCGA), p=0.72).

The second DPYD toxicity-associated variant (Table 6) was identified following SNP imputation in the region of 1.5 Mb surrounding rs7548189, a tagSNP intronic to DPYD (chr1:97,867,713, b37). rs7548189 was borderline associated with the binary measure global toxicity ($OR_{globalbinary}$=1.67, p=3.79×10$^{-5}$). Further investigation showed rs7548189 formally to be associated with the quantitative measure of global toxicity, and with diarrhea under both binary and quantitative models ($OR_{globalquant}$=1.23, p=6.82×10$^{-6}$, $OR_{diarrheaquant}$=1.18, p=1.54×10$^{-5}$; $OR_{diarrheabinary}$=1.76, p=1.72×10$^{-5}$). As can be seen from Table 6, HFS also contributed to the association with global toxicity. Following regional imputation, rs12022243 ($r^2$ with rs7548189=0.95) was found formally to be associated with global toxicity under a binary model ($OR_{globalbinary}$=1.69, p=2.55×10$^{-5}$). rs12022243 showed excellent imputation quality: of 190 independently-assessed individuals, only 4 (2%) genotypes were missing and all of the remaining genotypes were imputed correctly.

Although there is little evidence from ENCODE data that rs7548189 is functional, rs12022243 falls in a region of open chromatin that may have enhancer activity. rs7548189 was not associated with DPYD expression levels in lymphoblasts, fibroblasts, T-cells, adipose tissue, or skin on the Genevar database (p>0.07) (Nica A C et al., *Plos Genetics* 7(2) (2011); Stranger B E et al., *Plos Genetics* 8(4): 272-284 (2012); Dimas A S et al., *Science* 325(5945): 1246-1250 (2009), each incorporated herein by reference) or in colon tissue from TCGA (p=0.97). rs12022243 was absent from these datasets.

Using logistic regression analysis, it was found that both the rs12132152 and rs7548189/rs12022243 signals were independent of each other and of the known DPYD toxicity variants *2A (rs3918290) and 2846T>A (rs67373796) (FIG. 5b). Further analysis of haplotypes based on 81 tagSNPs in a 25 kb window either side of DPYD provided no further refinement of the rs12132152 and rs7548189/rs120222243 associations and showed no evidence of additional, independent association signals.

d. Refining the Toxicity Association at the TYMS and ENSOF1 Loci

Analysis was carried out to resolve the basis of known toxicity associations at TYMS (Table 6). This analysis identified a new TYMS/ENOSF1 SNP predictive of FU toxicity.

Figure 4B:
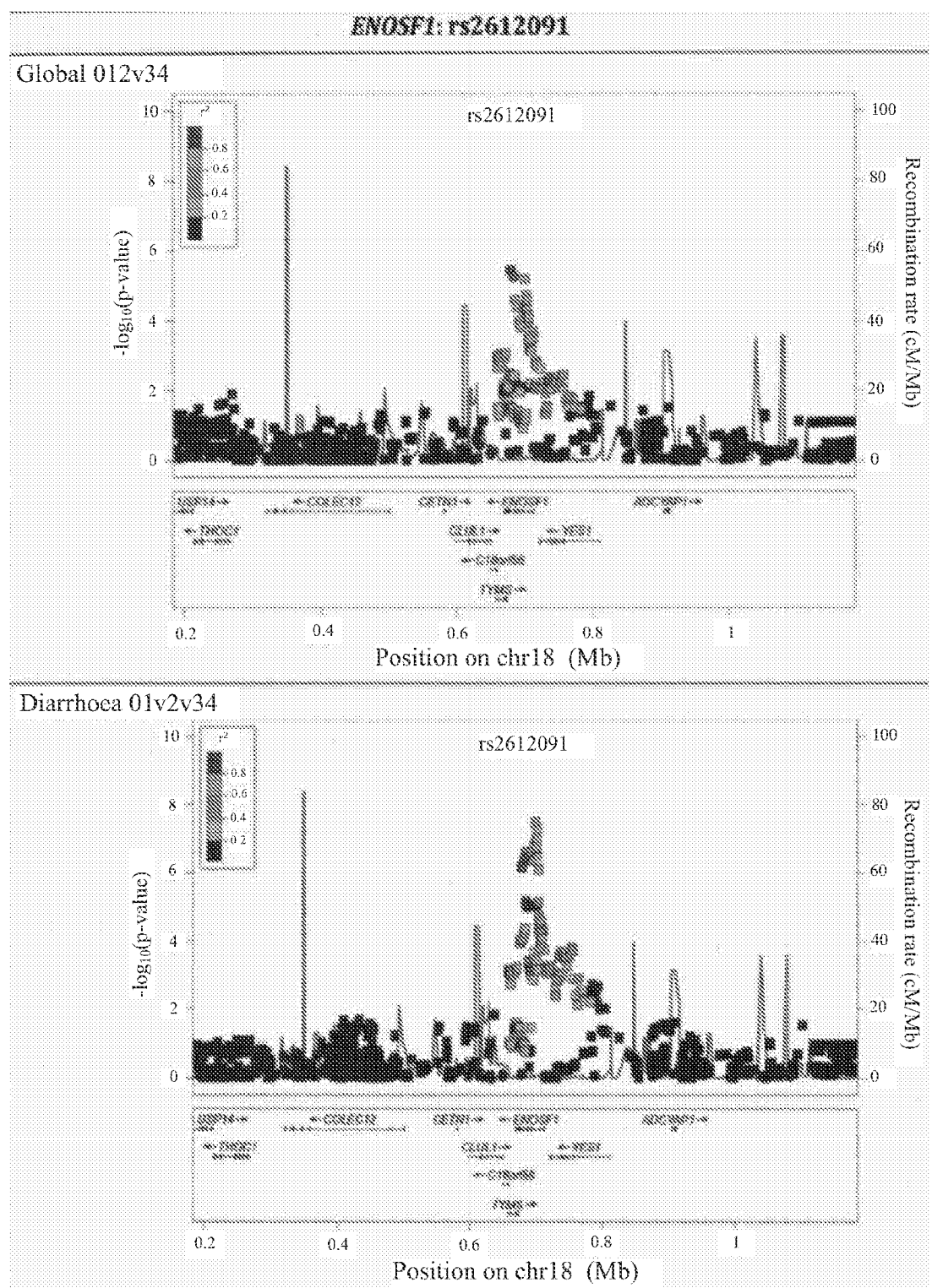

It was found that the G-allele (freq.=0.45) of SNP rs2612091 was associated with increased global toxicity ($OR_{globalbinary}=1.59$, $p=5.28\times10^{-6}$, $OR_{globalquant}=1.19$, $p=2.35\times10^{-6}$, Table 6). rs2612091 lies 10 kb downstream of TYMS within an intron of enolase superfamily member (ENOSF1, chr18:683,607). Fine mapping showed somewhat stronger associations for a SNP, rs2741171 (chr18:700, 687), in linkage disequilibrium ($r^2=0.73$) with rs2612091, particularly for the quantitative measure of global toxicity ($OR_{globalquant}=1.2$, $p=9.24\times10^{-7}$). The rs2741171 variant is further downstream of TYMS (27 kb) and again is intronic for ENOSF1, but both SNPs fall between recombination hotspots that flank the entirety of both TYMS and ENOSF1 (FIG. 4b). The rs2612091/rs2741171 effect on toxicity was essentially driven by HFS, with an especially strong association being observed using the quantitative measure (rs2612091: $OR_{hfsquant}=1.21$, $p=3.67\times10^{-7}$, rs2741171: $OR_{hfsquant}=1.23$, $p=3.10\times10^{-8}$).

ENOSF1 is a largely uncharacterized gene that appears to encode both a protein and RNAs antisense to TYMS. It has been proposed that ENOSF1 regulates TYMS mRNA and/or protein expression (Dolnick B J et al., *Cancer Biology & Therapy* 2: 364-369 (2003), incorporated herein by reference), and so the associations between rs2612091 genotype and TYMS and ENSOF1 expression were analysed using the Genevar and TOGA databases. Using Caucasian matched twin data from (Nica A C et al., *Plos Genetics* 7(2) (2011), incorporated herein by reference), the rs2612091 G-allele significantly decreased ENOSF1 expression in adipose tissue for both twin sets ($p_{set1}=7.0\times10^{-4}$, $p_{tset2}=9.7\times10^{-6}$) and in lymphoblastoid cells for one set ($p_{set1}=0.89$, $p_{set2}=0.0012$). However, rs2612091 genotype was not associated with TYMS expression (p>0.30 for each of the same analyses). Similarly, in lymphoblastoid expression data from (Stranger B E et al., *Plos Genetics* 8(4): 272-284 (2012), incorporated herein by reference), the rs2612091 G-allele was associated with decreased expression of ENOSF1 ($p=1.9\times10^{-6}$) but not TYMS ($p=0.82$). These results were replicated in the TOGA colon data, in which the rs2612091 G-allele was again associated with decreased ENOSF1 expression (OR=0.76, $p=1.5\times10^{-7}$), but not with TYMS (OR=0.95, $p=0.45$). It can be concluded that ENOSF1 is most likely to be the target of the functional variation tagged by rs2612091, and that this does not act through antisense-mediated down-regulation of TYMS, even though ENOSF1 and TYMS transcripts are overlapping.

The relationship was tested of the new TYMS/ENOSF1 toxicity SNP to two TYMS polymorphisms (5' VNTR 2R/3R and 3'UTR 6 bp ins-del (Schwab M et al., *J Clin Oncol.* 26(13): 2131-2138 (2008); Lecomte T et al., *Clin Cancer Res.* 10(17): 5880-5888 (2004), both incorporated herein by reference) that have previously been reported to alter TYMS expression and hence to affect 5-FU-related toxicity (Table 7). Noting moderate LD between rs2612091 and both the 5'VNTR and 3'UTR polymorphisms ($r^2=0.40$ and 0.32; FIG. 5), it was tested whether the rs2612091 signal was independent of the 5'VNTR and 3'UTR polymorphisms, using the quantitative measure of HFS (01v2v34) as the toxicity phenotype, because HFS underlies the global toxicity signal observed for all three variants.

First, the three variants were incorporated into a covariate-adjusted logistic regression model. Only rs2612091 remained significantly associated when adjusting for the other variants (for rs2612091 $OR_{hfsquant}=1.21$, p=0.00049, 5' VNTR p=0.19, 3'UTR p=0.48) Using rs2612091 alone in the model minimised the AIC.

Second, evidence of interaction (epistasis) among the variants was tested, but was found not to be significant between rs2612091 and either the 5'VNTR (p=0.92) or the 3'UTR (p=0.19). These analyses suggested that rs2612091 and the previously identified variants do not act as a 3-polymorphism tag for unidentified variants, and that rs2612091 better captures the association signal created by all three variants.

Finally, the independence of each variant in a 3-polymorphism haplotype (Table 7) was tested. It was found that the G-allele of rs2612091 consistently increased the risk of toxicity, irrespective of the 5'VNTR or 3'UTR genotype (p=0.0021). Conversely, neither the 5'VNTR (p=0.17) nor the 3'UTR (p=0.61) risk-allele consistently increased risk of toxicity when varying the genotype of the other two SNPs. The analysis was repeated as 2-polymorphism haplotypes comprising rs2612091 and either the 5'VNTR or 3'UTR variant. The rs2612091 genotype was again significantly associated with HFS, irrespective of either 5'VNTR (p=0.00053) or 3'UTR ($p=1.47\times10^{-6}$) genotype. The above analyses were repeated using global toxicity and results were similar, but reduced modestly in significance.

Equivalent logistic regression and haplotype analysis using the top fine-mapping SNP rs2741171 showed even stronger evidence that the new rs2612091 SNP signal alone explains the associations at TYMS/ENOSF1. The various combinations of rs2741171, rs2612091, 5'VNTR and 3'UTR polymorphisms were further tested in a multivariate logistic regression model and it was found that the model that minimised AIC incorporated rs2741171 alone. rs2741171 lies next to a region of open chromatin that may be a p300 binding site.

e. In Silico Replication Analysis in Additional Data Sets

The associations between toxicity and rs12132152, rs7548189 and rs2612091 were examined in 233 capecitabine-treated patients from the above-mentioned SCP study. Since these patients were selected from the extremes of the high- and low-toxicity distributions (Table 4), a formal meta-analysis was not performed. Moreover, a global measure of toxicity was not available and associations with the specific individual toxicities (diarrhea and/or HFS) that comprised the global association signals found in the QUASAR2 patients (Tables 6 and 8) were tested.

The ENOSF1/TYMS SNP rs2612091 was associated with HFS in SCP patients with an effect size similar to that in QUASAR2 ($OR_{binary}=1.6$, p=0.012). The DPYD region SNP, rs7548189 was associated with HFS in the SCP study ($OR_{binary}=1.7$, p=0.048), but showed no evidence of an association with diarrhea ($OR_{binary}=0.78$, p=0.46). Furthermore, rs7548189 was tested in 85 capecitabine-treated patients from the above-mentioned EPICOLON study (Abuli A, et al. *Carcinogenesis* (Epub ahead of print) (2013), incorporated herein by reference), and evidence of an association with severe diarrhea ($OR_{binary}$=1.47, P=0.020) was found.

The association between HFS and the relatively rare DPYD SNP rs12132152 was not replicated in the SCP set (Table 8), which showed an opposite direction of effect from that observed in QUASAR2 ($OR_{binary}$=0.30, p=0.025). Since the rs12132152 association in QUASAR2 was very strong, the absence of association in the SCP study data might result from genetic differences between the northern and southern European populations. Accordingly, the linkage disequilibrium structure of a 1 Mb region around rs12132152 in the 1000 genomes GBR (UK) and TSI (Tuscan) data sets was determined.

A set was found of 14 non-coding rare variants that were highly correlated with each other, were in moderate linkage disequilibrium with rs12132152 ($r^2$~0.5), their best tagSNP, in the GBR data, but showed almost no association with rs12132152 in the TSI data ($r^2$<0.002). All of the 14 variants had failed the imputation quality control checks for QUASAR2, but represent potential functional toxicity variants tagged by rs12132152. Of particular note, three of these variants (rs72724388, rs72724390 and rs142652198) lie within DPYD introns and are transcribed as part of an antisense mRNA (DPYD-AS1, chr1:97561479-97788511) that is uncharacterised in vivo.

f. Set-Based Tests

In order to determine whether there was evidence in QUASAR2 of additional toxicity associations that had not reached formal statistical significance for individual SNPs or rare variants, association tests were performed based on sets of variants (Table 9). Both the previously-reported toxicity variants and the variants of the invention were excluded, namely DPYD 2846,*2A variants, DPYD rs12132152, DPYD rs7548189 and TYMS rs2612091, as well as regions in linkage disequilibrium of $r^2$>0.1 with these SNPs (including the TYMS 5'VNTR and 3'UTR polymorphisms).

Using a false discovery rate of q=0.05, no convincing evidence was found for additional associations at any gene or in the set of variants as a whole. However, suggestive evidence exists of associations between variants at the TYMP locus and HFS and diarrhea (Table 9).

g. Identifying New, Rare Susceptibility Variants in DPYD and TYMS

Sequencing the coding regions of DPYD and TYMS identified only a single missense variant in the HiTox pool (DPYD c.G1651A; p.Ala551Thr, chr1:97981371) that was not present on SNP and exome arrays. No other occurrence of this variant was found in the full set of 968 patients. The mean number of sequencing reads per person for this variant was 70 and the overall variant read frequency was 0.0035. This variant (A551T) was predicted to be strongly damaging by SIFT, Polyphen, PhyloP, and MutationTaster. Sanger sequencing identified a single patient with this rare allele, who had experienced grade 4 neutropaenia and thrombocytopaenia.

Database searches determined that this variant has been previously reported as causal for DPYD Deficiency Syndrome (OMIM 612779) (Van Kuilenburg A B et al., *Biol Chem.* 386(4): 319-324 (2005), incorporated herein by reference). It was confirmed that A551T was not in linkage disequilibrium with any of the other common or rare DPYD toxicity variants.

Of the 19 patients with extreme (grade 4) toxicity at any cycle, it was determined which alleles they carried at the three toxicity SNPs and their complement of rare DPYD alleles from the literature, including 2846 A>T and *2A that were shown to be associated with 5-FU toxicity in our previous meta-analysis (Rosmarin et al., *Journal of clinical oncology: official journal of the American Society of Clinical Oncology* (2014), in press, incorporated herein by reference) (Table 10). There was no good evidence that the risk alleles at the 3 new toxicity SNPs were over-represented as a group in these 19 patients (Table 10). Using the evaluation of Caudle et al (Caudle et al., *Clinical pharmacology and therapeutics* 94(6):640-5 (2013), incorporated herein by reference) as a guide, supplemented by data from this study, the likely contributions of each rare DPYD variant to extreme toxicity were assessed. There was insufficient prior evidence (Caudle et al., *Clinical pharmacology and therapeutics* 94(6):640-5 (2013), incorporated herein by reference) to regard six DPYD alleles (*4, *5, *6, *9A, M166V and K259E) as pathogenic (Table 11). Inspection of the genotypes of these polymorphisms in the severe toxicity cases (Table 10) and the tests of association with binary global toxicity (Table 11) did not contradict this view.

Several other rare DPYD alleles (*3, *7, *8, *9B, *10, *11, *12) were not present in the sample set. Four rare DPYD alleles were denoted as severely functionally deleterious: *2A, 2846T>A, *13 and A551T. Five of 19 (26%) severe-toxicity patients carried one of these DPYD alleles (Table 10). Of these 5 cases, 4 (80%) had life-threatening bone marrow toxicity (G4 neutropaenia and thrombocytopaenia), whereas the other had G4 diarrhea. Another individual with G4 neutropaenia, but not thrombocytopaenia, did not carry any of the 4 DPYD alleles. Overall, for prediction of severe myelosuppression, the rare DPYD variants had 83% sensitivity, 99% specificity, 29% positive predictive value and 99.9% negative predictive value.

Like the other rare DPYD variants (*2A and 2846T>A) that have established associations with 5-FU-related toxicity in the heterozygous state, A551T has been shown to cause the recessive DPYD deficiency syndrome when present as the homozygote or compound heterozygote with another mutant allele (Schwab M et al., *J Clin Oncol.* 26(13): 2131-2138 (2008), incorporated herein by reference). The identification of A551T in a patient experiencing grade 4 neutropaenia and thrombocytopaenia further supports the view that rare non-synonymous DPYD variants that cause DPYD Deficiency Syndrome—such as 1560S and about 15 others (Van Kuilenburg A B et al., *Biol Chem.* 386(4): 319-324 (2005); Van Kuilenburg A B et al., *Hum Genet.* 104(1): 1-9 (1999); Van Kuilenburg A B et al., *Biochem J* 364: 157-163 (2002), each incorporated herein by reference)—greatly increase the risk of 5-FU toxicity in heterozygotes.

Furthermore, of the three other QUASAR2 patients who experienced grade 4 myelotoxicity—two of whom were the only toxicity-induced deaths in QUASAR2—one carried DPYD *2A, one 2846A>C and one *13. Of the 12 carriers of rare, functionally-deleterious DPYD alleles who did not develop severe toxicity, 7 suffered a grade 3 toxicity and may therefore have been spared severe toxicity by capecitabine dose reduction. Thus, it is plausible that extreme capecitabine/5-FU-related toxicity is heritable.

h. Receiver Operating Characteristics (ROC) Analysis

In order to test the performance of a model to predict 5-FU toxicity based on the previously-reported capecitabine toxicity variants and the newly identified variants of the invention, the QUASAR2 data set and DPYD 2846T>A, DPYD *2A, DPYD rs12132152, DPYD rs7548189, DPYD p.Ala551Thr, and TYMS rs2612091 variants were incorporated into a ROC analysis for prediction of global grade 012v34 capecitabine-related toxicity. Such a model tests the clinical utility of the invention.

938 patients were analysed, applying a score for each patient that summed:

(number of harmful alleles at each polymorphism)×
(beta coefficient per allele)

The DPYD variants rs12132152, rs7548189 and A551T were assumed to be functionally equivalent and hence combined for the purposes of this analysis into a test of any rare functional allele versus no rare allele (OR=7.6, p=4.5× $10^{-4}$). The area under curve (AUC) was found to be 0.66 (95% CI 0.63-0.70). At the cut-off for which the maximum proportion of patients were correctly classified (69%), sensitivity was 27% (95% CI 23-33%), specificity was 91% (95% CI 88-93%), positive predictive value was 60% (PPV: 95% CI 52-68%), and negative predictive value was 71% (NPV: 95% CI 68-74%) (FIG. 6).

The invention claimed is:

1. A method, comprising: isolating a sample, and detecting in the sample by an assay:
    (a) a thymidylate synthase (TYMS) polymorphisms rs2612091 and
    (b) at least one dihydropyrimidine dehydrogenase (DPYD) polymorphism selected from the group consisting of: rs3918290, rs67376798, rs12132152, rs12022243 and substitution of guanine for adenine at coding DNA position 1651 (C.G1651A).

2. The method according to claim 1, wherein the detecting comprises
    detecting the TYMS polymorphism rs2612091; and
    detecting DPYD polymorphisms rs3918290, rs67376798, rs12132152, and c.G1651A.

3. The method according to claim 1, wherein the sample is obtained from a cancer patient.

4. The method according to claim 1, wherein the sample is obtained from a subject who is undergoing chemotherapy with 5-fluorouracil (FU).

5. The method according to claim 4, wherein the subject is undergoing capecitabine monotherapy.

6. The method according to claim 1, wherein the sample is a fluid sample from a patient.

7. The method according to claim 6, wherein the fluid sample is a saliva, blood serum or plasma sample.

8. The method according to claim 1, wherein the sample is a solid sample from a patient.

9. The method of claim 1, wherein the sample is obtained from a patient, and
    the method further comprises administering a chemotherapeutic agent that does not comprise 5-fluorouracil.

* * * * *

UNITED STATES PATENT AND TRADEMARK OFFICE
CERTIFICATE OF CORRECTION

PATENT NO. : 10,774,385 B2
APPLICATION NO. : 15/123620
DATED : September 15, 2020
INVENTOR(S) : David Kerr et al.

Page 1 of 1

It is certified that error appears in the above-identified patent and that said Letters Patent is hereby corrected as shown below:

In the Claims

Column 31, Line 23, Claim 1, please delete "polymorphisms" and insert --polymorphism--

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*